(12) United States Patent
Ullrich et al.

(10) Patent No.: US 8,277,802 B2
(45) Date of Patent: Oct. 2, 2012

(54) DIAGNOSIS AND PREVENTION OF CANCER CELL INVASION

(75) Inventors: Axel Ullrich, Munich (DE); Pjotr Knyazev, Gauting (DE); Tatjana Knyazeva, Gauting (DE); Yuri Cheburkin, Munich (DE); Peter Vajkoczy, Mannheim (DE)

(73) Assignee: Max-Planck-Gesellschaft zur Foederung der Wissenschaften e.V., Munich (DE)

( * ) Notice: Subject to any disclaimer, the term of this patent is extended or adjusted under 35 U.S.C. 154(b) by 155 days.

(21) Appl. No.: 10/521,410

(22) PCT Filed: Jul. 17, 2003

(86) PCT No.: PCT/EP03/07786
§ 371 (c)(1),
(2), (4) Date: Jan. 18, 2005

(87) PCT Pub. No.: WO2004/008147
PCT Pub. Date: Jan. 22, 2004

(65) Prior Publication Data
US 2005/0186571 A1    Aug. 25, 2005

(30) Foreign Application Priority Data
Jul. 17, 2002  (EP) ................................. 02015944

(51) Int. Cl.
*A61K 39/395* (2006.01)
*A61K 39/00* (2006.01)

(52) U.S. Cl. ............. 424/130.1; 424/135.1; 424/141.1; 424/143.1; 424/154.1; 424/152.1; 424/155.1; 424/156.1

(58) Field of Classification Search ........................ None
See application file for complete search history.

(56) References Cited

U.S. PATENT DOCUMENTS

| | | | | |
|---|---|---|---|---|
| 5,468,634 | A | * | 11/1995 | Liu ................................ 435/348 |
| 5,538,861 | A | * | 7/1996 | Schneider et al. ........... 435/69.1 |
| 2004/0180002 | A1 | * | 9/2004 | Young et al. ................. 424/1.49 |
| 2006/0019256 | A1 | * | 1/2006 | Clarke et al. .................... 435/6 |

FOREIGN PATENT DOCUMENTS

| | | |
|---|---|---|
| WO | 89/06692 A1 | 7/1989 |
| WO | WO 89/06692 A1 * | 7/1989 |
| WO | 92/17608 | 10/1992 |
| WO | 98/06692 | 2/1998 |
| WO | 00/76309 A2 | 12/2000 |
| WO | WO 01/30964 A2 * | 5/2001 |
| WO | WO 01/48190 A2 * | 7/2001 |
| WO | 01/78778 A1 | 10/2001 |
| WO | 02/46467 A2 | 6/2002 |

OTHER PUBLICATIONS

Meric et al. (Clinical Cancer Research, vol. 8, pp. 361-367, Feb. 2002).*
Freshney (Culture of Animal Cells, A Manual of Basic Technique, Alan R. Liss, Inc., 1983, New York, p. 4).*
Dermer (Bio/Technology, 1994, 12:320).*
Drexler et al (Leukemia and Lymphoma, 1993, 9:1-25).*
Zellner et al (Clin. Can. Res., 1998, 4:1797-1782).*
Jain (Sci. Am., 1994, 271:58-65).*
Curti (Crit. Rev. in Oncology/Hematology, 1993, 14:29-39).*
Taber's Cyclopedic Medical Dictionary (1985, F.A. Davis Company, Philadelphia, p. 274).*
Kaiser (Science, 2006, 313, 1370).*
Zips et al (In vivo, 2005, 19:1-7).*
Greenbaum et al. (Genome Biology, 2003, vol. 4, Issue 9, pp. 117.1-117.8).*
Hell et al. (Laboratory Investigation, 1995, 73: 492-496).*
Fu et al. (EMBO J., 1996, 15:43982-4401).*
Vallejo et al. (Biochimie, 2000 82:1129-1133).*
Jang et al. (Clinical Exp. Metastasis, 1997, 15: 469-483).*
Gura (Science, 1997, 278:1041-1042).*
Krontiris and Capizzi (Internal Medicine, 4th Edition, Editor-in-chief Jay Stein, Elsevier Science, 1994 Chapters 71-72, pp. 699-729).*
Carter, S. K. et al. Chemotherapy of Cancer; Second edition; John Wiley & Sons: New York, 1981; appendix C.*
Gura (Science, 1995, 270:575-577).*
Scherer and Rossi (Nature Biotechnology 2003, 21: 1457-1465).*
Verma et al. ((1997) Nature 389: 239-242).*
Marshall ((1995) Science, 269: 1050-1055).*
Eck et al. (Goodman & Gilman's The Pharmacological Basis of Therapeutics (1996), 9th Edition, Chapter 5, McGraw-W, NY).*
Rubanyi (Mol. Aspects Med. (2001) 22:113-142).*
Juengst (British Medical Journal (2003) vol. 326, pp. 1410-1411).*
Jacob et al. (Cancer Detection and Prevention 1999, 23:325-332).*
Meric et al., "Expression profile of tyrosine kinases in breast cancer", Clinical Cancer Research, 8/2 (361-367), Feb. 2002.
Bachmeier Beatrice E et al: "Matrix metalloproteinases (MMPs) in breast cancer cell lines of different tumorigenicity." Anticancer Research, vol. 21, No. 6A, Nov. 2001, pp. 3821-3828, XP008006514 ISSN: 0250-7005.
Attar, E. C. et al: "Axl receptor tyrosine kinase expression in human breast cancer." Breast Cancer Research and Treatment, (Oct. 1997) Vol. 46, No. 1, pp. 91 Meeting Info.: 20TH Annual San Antonio Breast Cancer Symposium San Antonio, Texas, USA Dec. 3-6, 1997, Oct. 1997, XP008006520.
Dodge Zantek N. et al: "MCF-10A-NeoST: A new cell system for studying cell-ECM and cell-cell interactions in breast cancer." Clinical Cancer Research, 7/11 (3640-3648)., Nov. 2001, XP001074226 * p. 3646, right-hand column, paragraph 5-p. 3647, left-hand column *.
Fridell Yih-Woei C et al: "GAS6 induces Axl-mediated chemotaxis of vascular smooth muscle cells" Journal of Biological Chemistry, American Society for Biochemistry and Molecular Biology, Baltimore, MD, US, vol. 273, No. 12, Mar. 20, 1998, pp. 7123-7126, XP002154999 v ISSN: 0021-9258.

(Continued)

*Primary Examiner* — Peter J Reddig
(74) *Attorney, Agent, or Firm* — Rothwell, Figg, Ernst & Manbeck, P.C.

(57) ABSTRACT

The present invention relates to diagnostic and therapeutic methods in the field of malignant disorders. Most particularly, the invention provides methods of determining the invasivity of malignant disorders and methods for reducing the invasivity of malignant disorders including the prevention or treatment of cancer cell invasion.

9 Claims, 16 Drawing Sheets

OTHER PUBLICATIONS

Figure 1:
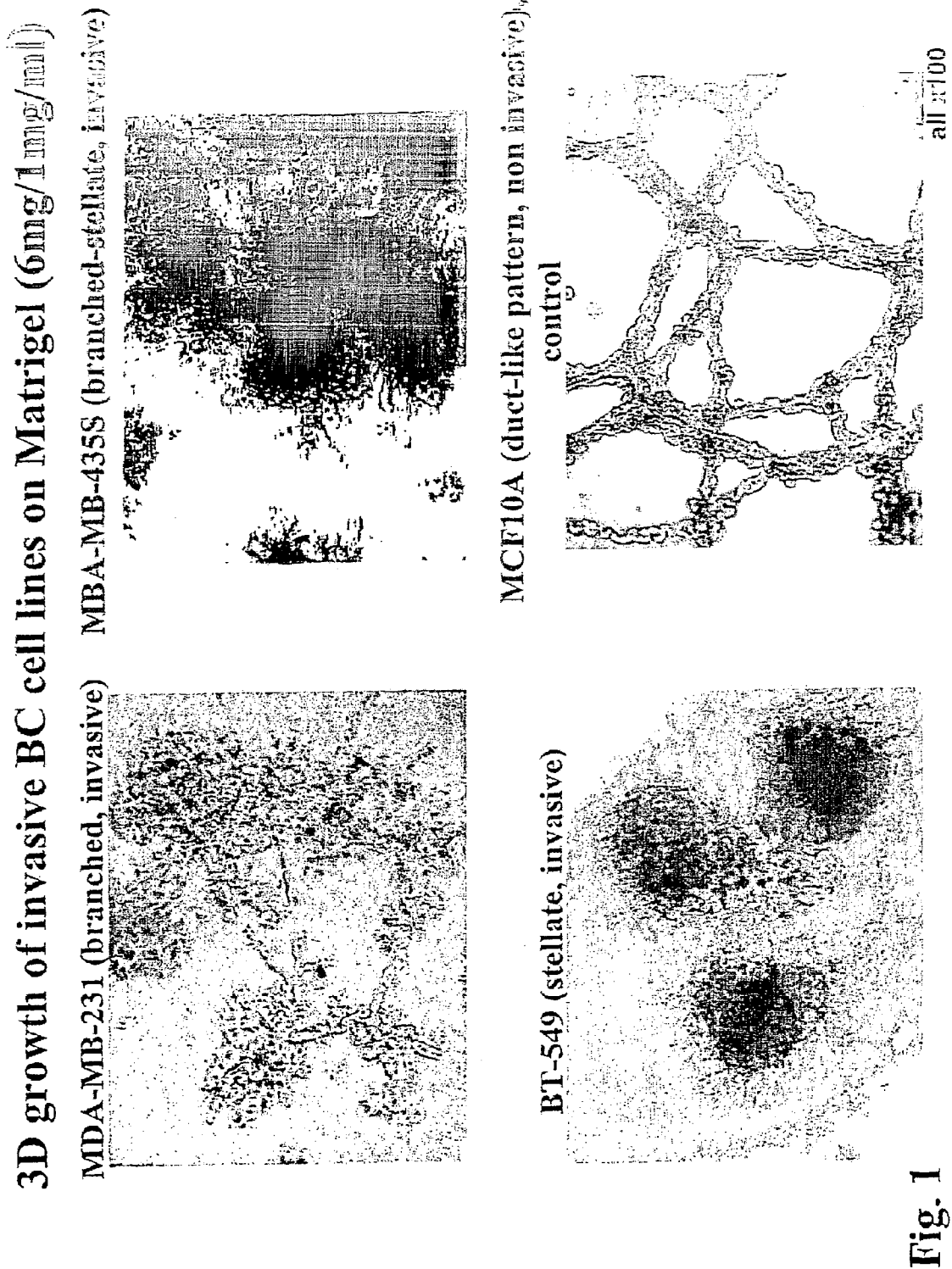

Wu Chew-Wun et al: "Clinical significance of AXL kinase family in gastric cancer." Anticancer Research, 22 (2B) 1071-8., Mar. 2002-Apr. 2002 XP008006835 p. 1075, left-hand column, paragraph 2-p. 1076, left-hand column, paragraph 2.

Meric F. et al: "Expression profile of tyrosine kinases in breast cancer." Clinical Cancer Research, 8/2 (361-367)., Feb. 2002, XP001074227 p. 366, left-hand column, paragraph 2.

Berclaz G et al: "Estrogen dependent expression of the receptor tyrosine kinase axl in normal and malignant human breast." Annals of Oncology, 12 (6) 819-24., Jun. 2001, XP008006834 p. 821, left-hand column, paragraph 2-p. 822, right-hand column, paragraph 1.

Krupitza G et al: "Genes Related to Growth and Invasiveness Are Repressed by Sodium Butyrate in Ovarian Carcinoma Cells" British Journal of Cancer, Nature Publishing Group, London, GB, vol. 73, No. 4, Feb. 1, 1996, pp. 433-438, XP000574908 ISSN: 0007-0920 * p. 435, col. 1, paragraph 6-col. 2, paragraph 1; figure 3 *.

Ito M et al: "Expression of Receptor-Type Tyrosine Kinase, Axl, and Its Ligand, GAS6, in Pediatric Thyroid Carcinomas Around Chernobyl" Thyroid, Mary Ann Liebert, New York, NY, US LNKD-DOI:10.1089/105072502320908303, vol. 12, No. 11, Nov. 1, 2002, pp. 971-975, XP008026096 ISSN: 1050-7256.

Sasaki T et al: "Crystal structure of a C-terminal fragment of growth arrest-specific protein Gas6. Receptor tyrosine kinase activation by laminin G-like domains" Journal of Biological Chemistry, American Society for Biochemistry and Molecular Biology, Inc, US LNKD DOI:10.1074/JBC.M207340200, vol. 277, No. 46, Nov. 15, 2002, pp. 44164-44170, XP001168602 ISSN: 0021-9258.

Pedrocchi M et al: "Expression of CA2+-Binding Proteins of the S100 Family in Malignant Human Breast-Cancer Cell Lines and Biopsy Samples" International Journal of Cancer, John Wiley & Sons, Inc, United States, Switzerland, Germany LNKD D01:10.1002/IJC.2910570513, vol. 57, No. 5, Jun. 1, 1994, pp. 684-690, XP001064860 ISSN: 0020-7136.

Domagala W et al: "Vimentin is preferentially expressed in human breast carcinomas with low estrogen receptor and high Ki-67 growth fraction", American Journal of Pathology, vol. 136, No. 1, 1990, pp. 219-227, XP008006515, ISSN: 0002-9440.

Chen, et al., "Global Analysis of Gene Expression in Invasion by a Lung Cancer Model," Cancer Research, 61, Jul. 1, 2001, pp. 5223-5230.

Gupta, R. et al.: "Receptor tyrosine kinase mutations in myeloid neoplasms", British Journal of Haematology, Wiley-Blackwell Publishing Ltd., vol. 117, No. 3, Jun. 1, 2002, pp. 489-508.

Yanagita, M. et al., "Gas6 regulates mesangial cell proliferation through Axl in experimental glomerulonephritis", American Journal of Pathology, American Society for Investigative Pathology, vol. 158, No. 4, Apr. 2001, pp. 1423-1432.

* cited by examiner

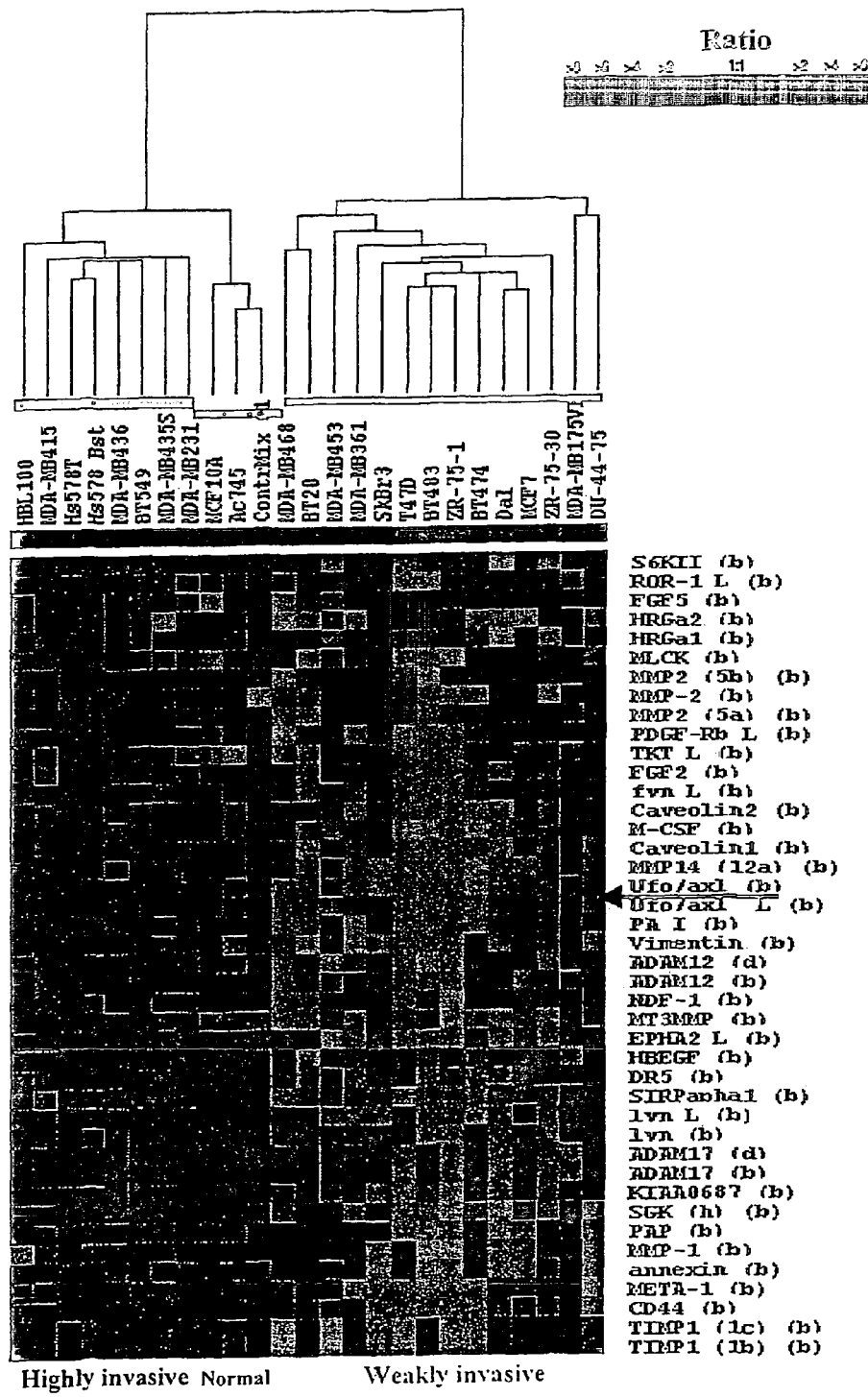

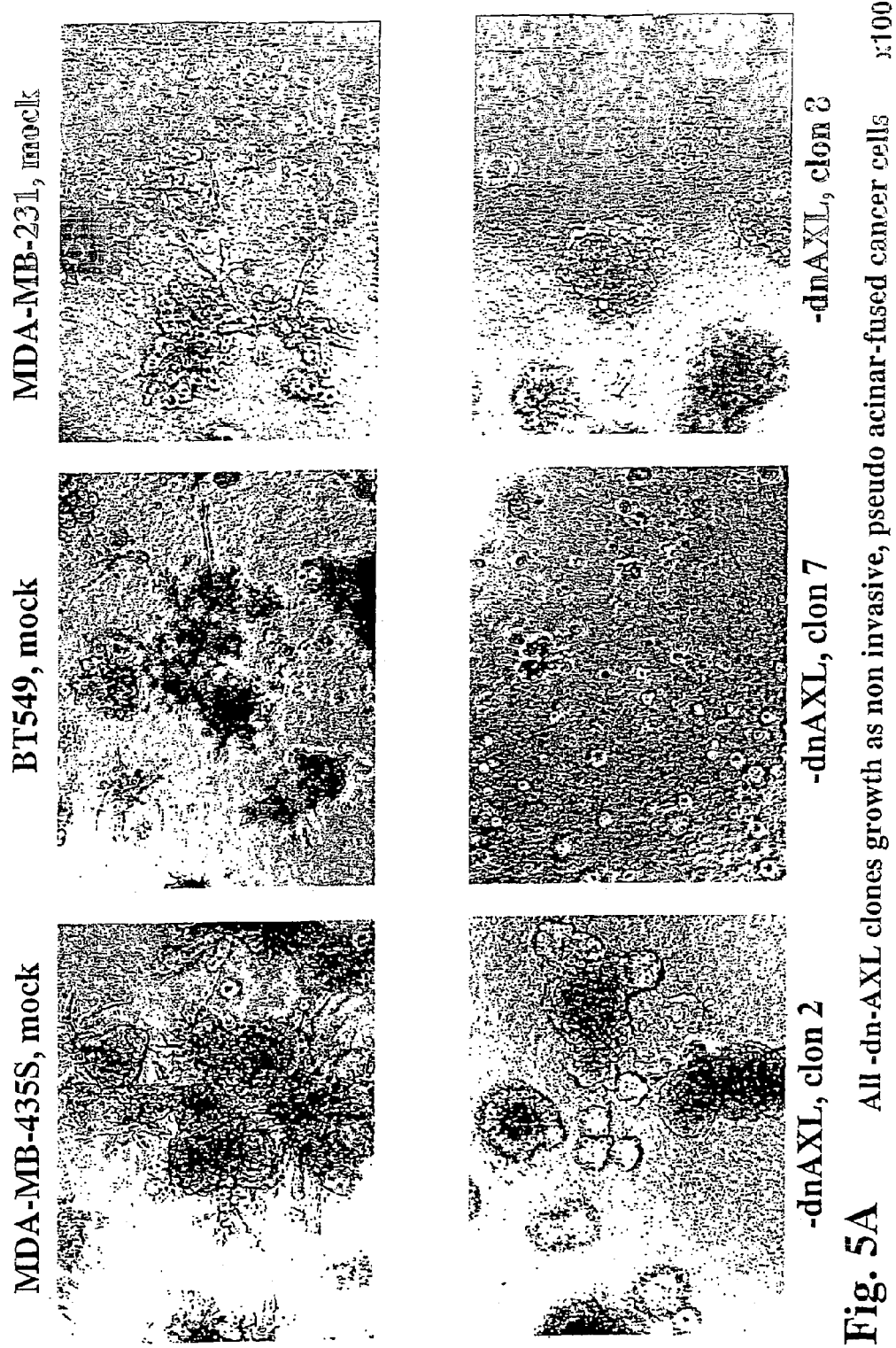
Fig. 5A All -dn-AXL clones growth as non invasive, pseudo acinar-fused cancer cells Fig. 5B   Wound assay
MDA-MB-435S, mock    10%FCS    MDA-MB435S-dnAXL, cl. 2
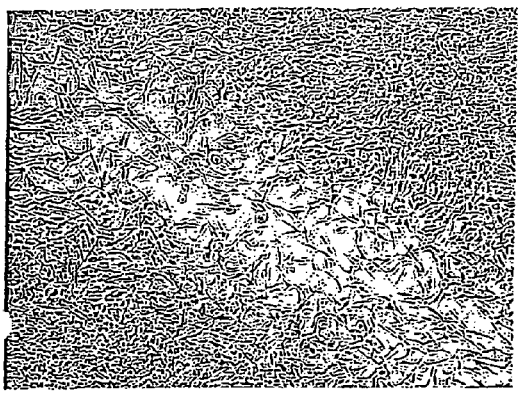
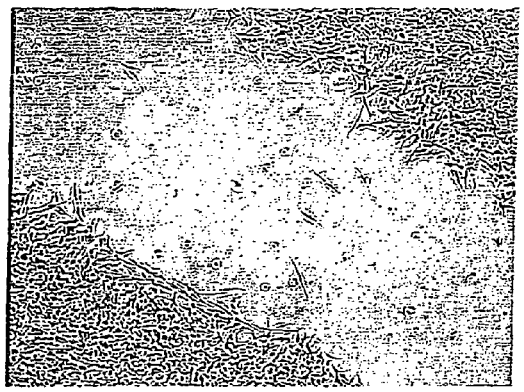
FCS+GAS6
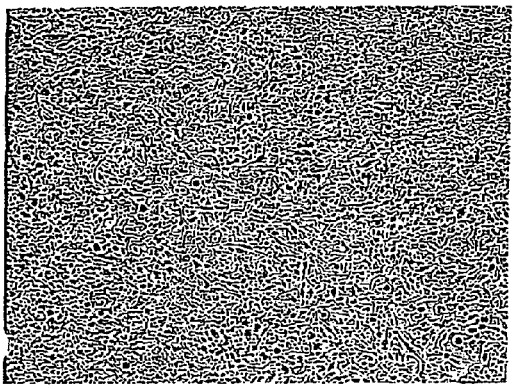
Starvation 72h
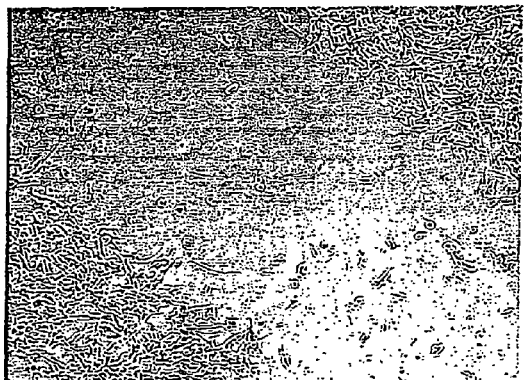

DIAGNOSIS AND PREVENTION OF CANCER CELL INVASION

CROSS REFERENCE TO RELATED APPLICATION

This application is a 35 USC §371 National Phase Entry Application from PCT/EP2003/007786, filed Jul. 17, 2003, and designating the U.S.

The present invention relates to diagnostic and therapeutic methods in the field of malignant disorders. More particularly, the invention provides methods of determining the invasivity of malignant disorders and methods for reducing the invasivity of malignant disorders including the prevention or treatment of cancer cell invasion.

In recent years it has been shown that overexpression of receptor tyrosine kinases (RTK) is in many cases associated with the development of malignant disorders, particularly cancer in mammals including, human beings. For example, overexpression of the receptor tyrosine kinase AXL/UFO (ref. 1, 2; Genbank accession No. M 76125) has been implicated in the development of human hematological malignancies. Further, very recent data indicate that signalling of AXL and its ligand GAS6 is involved in angiogenesis, adhesion and survival of cancer cells (ref. 3, 4, 5, 6, 7, 8). In Breast Cancer Research and Treatment (October 1997), Vol. 46, No. 1, pp. 91, Attar, E. C. et al. disclose studies on AXL receptor tyrosine kinase expression in human breast cancer (ref. 33). Dodge Zantek N. et al. have presented MCF-10A-NeoST as a new cell system for studying Cell-ECM and Cell-Cell interactions in breast cancer (ref. 34). They suggest a potential role of AXL in the invasiveness and as a progressing factor for breast cancer. There are, however, no data presented which would demonstrate that overexpression of AXL is correlated with the invasivity and/or metastasis formation in other malignant disorders.

One purpose of the present study was to establish expression profiles of genes particularly selected from protein kinases, phosphatases and other signalling genes in malignant disorders, particularly breast cancer and brain cancer in order to identify novel markers for invasivity and/or aggressiveness. A cDNA hybridization array was used to analyze gene expression profiles of seven highly invasive, fourteen weakly invasive breast cancer cell lines and three normal breast epithelial cell lines. Differences in gene expression between weakly and highly invasive breast cancer cell lines were identified, which enable the definition of a gene cluster correlating with the invasivity of a breast cancer cell line. By using this cluster or combinations of genes therefrom, a discrimination of highly invasive breast cancer cell lines from weakly invasive breast cancer cell lines and normal breast epithelial cell lines is possible.

Further, in an attempt to identify novel receptor tyrosine kinases (RTK) involved in the biology of malignant glioma, the RTK expression profile in human glioma cell lines has been determined by a cDNA microarray technique. Besides EGFR and PDGFR-α, the receptor UFO/AXL was one of the most prominently expressed RTKs. In 7/9 human glioma cell lines tested, UFO/AXL mRNA had a higher expression level than the mRNA for EGFR (Table 4). Inhibition of UFO/AXL signal transduction by overexpressing a truncated, dominant-negative mutant form of UFO/AXL suppressed tumor progression and prolonged survival in mice when compared to cells overexpressing the UFO/AXL wild-type form. In order to study the mechanism of UFO/AXL signalling and its role in glioma growth, tumor cell morphology and tumor cell behavior with respect to proliferation, aggregability, migration, and invasion were assessed in vitro. Furthermore, tumor cell behavior, tumor angiogenesis, and tumor perfusion were analysed in vivo by intravital multi-fluorescence microscopy. The study indicates a novel role for UFO/AXL, i.e. in mediating glioma cell-cell interactions, glioma cell migration and glioma invasion. UFO/AXL is the first RTK to be implemented in mediating the diffuse-infiltrative, local metastatic growth of malignant brain tumors.

Thus, a first aspect of the present inventions relates to a method of determining the invasivity of malignant disorders comprising determining the expression of at least one gene selected from the group consisting of AXL (Genbank M 76125), GAS 6 (Genbank L 13720), MMP14 (Genbank NM 004995), ADAM12 (Genbank AF 023476), ADAM17(Genbank U 69611), MT3MMP (Genbank NM 005961), FGF2 (Genbank NM 002006), FGF5 (Genbank NM 004464), FYN (Genbank M 14333), LYNN (Genbank M 16038), DDR2 (Genbank X 74764), TIMP1 (Genbank NM 003254), HB-EGF (Genbank NM 001945), SGK (Genbank Y 10032), RPS6RB1 (Genbank M 60724), MAP4K4 (Genbank XM 038748), SIRPα (Genbank Y 10375) and Annexin A2 (Genbank D 00017). Further, the expression of the genes Stat 5b (Acc. NM_012448) or EDG2 (Acc. NM_057159) may be determined as indicator for the invasivity of malignant disorders, optionally in addition to determining the expression of one or more of the above genes. It was found that a high expression of at least one of the above genes correlates with a high invasivity.

Further, within the present studies a high invasivity was found to correlate with a high expression of at least two of the above genes, in particular AXL and one or more further genes. The one or more further genes can be selected from the genes listed above or from a gene which is already known as a marker for invasiveness.

Thus, the method preferably comprises, determining the expression of several of the above genes, e.g. determining the expression of at least two, three, four, five, six, seven or eight genes. More preferably, the method comprises determining the expression of at least the AXL/UFO gene (Genbank M 76125). Further, the method may comprise determining the expression of at least one further gene which is a already known as a marker of invasiveness, such as CD44 (Genbank X 66733), vimentin (Genbank X 56134), CAV1 (Genbank Z 18951), CAV2 (Genbank AF 03572), MMP 1 (Genbank M 13509), MMP 2 (Genbank NM 004530), MMP9 (Genbank NM 004994), M-CSF (Genbank MA 37435) and EPHA2 (Genbank M 59371).

A correlation between expression of the above gene cluster and particularly the AXL gene and invasivity was found in several types of malignant disorders, e.g. breast cancer, particularly primary breast cancer, prostate cancer, kidney cancer and glioblastomas or other cancers of epithelial origin. Of particular interest is the finding that a correlation exists between expression of one or more of the above marker genes and in particular of the AXL gene and invasivity of glioblastomas.

Further, it was found that stable overexpression of a dominant negative mutant of the AXL gene is capable of strongly suppressing cell invasiveness and migration indicating that inhibition of AXL function may block and loss of metastasis formation in highly invasive malignant disorders, such as breast cancer or brain cancer, e.g. glioblastoma. Furthermore, a polyclonal antibody directed against the extracellular portion of AXL has a very strong inhibitory activity on the migration and invasivity of cancer cells, e.g., breast or prostate cancer cell lines. Moreover, overexpression of wildtype AXL in weakly invasive breast cancer, prostate cancer cell lines and glioma cells significantly increased their invasivity.

These data show that the AXL gene and protein is a promising new target for the prevention or treatment of malignant disorders, particularly for inhibiting the tumor invasivity and/or metastasis formation in malignant disorders.

Thus, a further aspect of the present invention relates to a method of reducing the invasivity of malignant disorders comprising inhibiting the AXL gene, AXL ligand gene or protein, or ligand thereof. The method may comprise (i) inhibiting the receptor tyrosine kinase activity of the AXL protein, (ii) inhibiting the expression of the AXL gene, (iii) inhibiting the interaction between the AXL protein and its ligands, particularly GAS6 and/or (iv) inhibiting the interaction of AXL with downstream signal transducing factors.

With respect to AXL protein ligands, laminin G-like domains of GAS6 (GAS6-LG) in particular have been found to be involved in the interaction with the AXL protein, such as AXL binding and activation (Reference 36). In particular, residues of the GAS-LG2 domain, for example Leu$^{620}$, Tyr$^{660}$ and Phe$^{487}$, affect AXL binding and/or activation. According to a specific embodiment of the invention, the method of reducing invasivity of malignant disorders comprises the inhibition of one or more residues of the GAS6-LG, in particular Leu$^{620}$, Tyr$^{660}$ and/or Phe$^{487}$.

The present invention relates to the diagnosis or the prevention and/or treatment of malignant disorders, particularly the tumor invasivity and/or metastasis formation in malignant disorders. Preferred examples of malignant disorders are cancers of the breast, prostate, kidney, colon, lung and glioblastomas. More preferably, the malignant disorder is breast cancer or glioblastomas.

In the diagnostic embodiment of the present invention the expression of invasivity-associated genes is determined qualitatively and/or quantitatively. The expression is determined in a sample comprising malignant cells, e.g. from a human tumour patient. The sample may be derived from tissue sections, biopsy samples etc. or from body fluids. Gene expression in the sample to be tested may be compared with gene expression in control samples, e.g. negative control samples from "normal" cells or weakly invasive malignant cells, and/or from positive controls, e.g. from highly invasive malignant cells.

Gene expression may be determined according to methods known in the art, e.g. on the mRNA or transcript level and/or on the protein level.

Measurement of gene expression on the mRNA level may comprise reverse transcription and/or amplification reactions such as PCR. Preferably, gene expression is measured on a nucleic acid array, wherein nucleic acids from the sample to be tested, e.g. RNA or cDNA, is hybridized to an array of immobilized probes specific for the nucleic acids to be tested. A preferred example of a suitable nucleic acid array is described in PCT/EP 02/01073. Alternatively, gene expression may be determined by other methods, e.g. Northern blot hybridization.

Gene expression on the protein level may be determined by immunological methods using antibodies directed against the proteins encoded by invasivity-associated genes. The antibodies may be labeled directly or indirectly by known, labeling groups such as radioactive, fluorescence, chemiluminescence or enzymatic groups such as known in the art.

The therapeutic embodiment of the present invention particularly relates to a method comprising the administration of an inhibitor of the AXL gene, AXL ligand gene, AXL protein or ligand thereof in an amount which is effective of reducing the invasivity of malignant disorders to a subject in need thereof. The subject is preferably a mammal, more preferably a human being. The ligand of the AXL protein is preferably GAS6, in particular residues of GASG-LG, as defined above.

The inhibitor of the AXL gene, AXL ligand gene, AXL protein or ligand thereof, e.g. GAS6, may be an antibody, a biologically active nucleic acid or a low molecular weight compound, e.g. a peptide or a non-peptidic organic compound.

In a preferred embodiment the inhibitor is an antibody directed against the AXL protein or a ligand thereof, e.g. GAS6. The term "antibody" relates to polyclonal antibodies and monoclonal antibodies, particularly to chimeric or humanized monoclonal antibodies or to human antibodies. Further, the term comprises antibody fragments, e.g. proteolytic fragments such as Fab, Fab' or F(ab)$_2$ fragments or recombinant fragments such as single chain antibody fragments, e.g. scFv fragments. Methods of manufacturing antibodies or antibody fragments as described above are known in the art.

In a further preferred embodiment the inhibitor is a biologically active nucleic acid, e.g. a DNA, an RNA or a synthetic nucleic acid analog. Preferred examples of biologically active nucleic acids are antisense nucleic acids, ribozymes or RNA interference molecules directed against the AXL gene or an AXL ligand gene or a transcript thereof. A further preferred example of a biologically active nucleic acid is a dominant-negative mutant of the AXL gene. Biologically active nucleic acids may be delivered by known procedures, e.g. by using viral or non-viral gene transfer vectors.

In a still further preferred embodiment the inhibitor is a peptidic compound, e.g. a peptide having a length of from 4 to 25 amino acids, a cyclic peptide, a peptide, derivative or a peptide mimetic derived from such a peptide. Alternatively the low-molecular weight inhibitor may be a non-peptidic, organic compound, e.g. an inhibitor of AXL kinase activity. Low-molecular weight inhibitors may be obtained by screening suitable compound libraries in a method as described, in more detail below.

Still a further aspect of the present invention relates to a pharmaceutical composition comprising as an active agent an inhibitor of the AXL gene, AXL ligand gene, AXL protein or ligand thereof (e.g. GAS6, in particular residues from GAS6-LG, as defined above) together with pharmacologically active diluents, carriers and/or adjuvants. This composition is particularly suitable for reducing the invasivity of malignant disorders and/or reducing the metastasis formation in malignant disorders. Depending on the type of inhibitor used as an active agent, the pharmaceutical composition may be a liquid, a solid, e.g. a powder, tablet etc., an emulsion or a suspension. The composition may be administered by injection, orally, topically, rectally, intranasally or by any other suitable means. The effective amount of the active agent in the composition may be determined by the skilled person without any undue burden depending on the type of compound and the disease to be treated.

The composition may comprise at least one further active agent. This at least one further active agent may be formulated together with the AXL inhibitor in a single composition or in a separate composition which is coadministered with the AXL inhibitor composition. The further active agent may be a cytotoxic or cytostatic agent such as doxorubicin cis-platin, carboplatin, an anti-tumor antibody or any combination thereof.

Still a further aspect of the invention relates to a method of identifying and/or characterizing an inhibitor of the invasivity of malignant disorders comprising determining, if at least a test compound is capable of inhibiting the AXL gene, AXL ligand gene, AXL protein or ligand thereof (e.g. GAS6 as defined above) or protein. More particularly, the method comprises determining, if a test compound is capable of binding to the AXL protein and/or reducing the AXL gene expression. The test compound may be derived from compound libraries, e.g. peptide or non-peptidic libraries which are subjected to a screening for AXL inhibitory activity. The screening method may comprise the use of a cell-based assay system, e.g. a system using a cell capable of overexpressing the AXL gene. Additionally or alternatively, the method may comprise the use of a cell-free assay system, wherein the test compound is contacted with substantially purified AXL protein or a fragment thereof in order to determine binding of the test compound to the protein or fragment thereof.

Further, the invention shall be explained in more detail by the following figures and examples.

FIG. 1. Morphology of normal and breasts carcinoma cell lines when cultured on matrigel-matrix (3D outgrowth).

Cells were cultured on top of a Matrigel layer for 7-14 days. A, photographs representing the three basic morphologies are shown for the indicated BC cell lines. Magnification was ×100 for MDA-MB-231, MDA-MB-435S, BT549 and MCF10A. Determination of the morphology of cells grown on Matrigel was carried out as described previously (10, 11, 12). Briefly, cells (5000 cells/well of a 96-well plate) resuspended in 50 µl of culture medium were plated on top of a preset Matrigel coating consisting of 70 µl of Matrigel (Becton Dickinson) diluted to 6 mg/ml in RPMA basal medium salts. After polymerization on the top those 50 µl of Matrigel (1.0 mg/ml) was added. Colony outgrowth was monitored over the course of the experiment and photographed at 7-14 days using a Zeiss Axiovert 35 microscope equipped with OpenLab (UK) digital camera. The name of the respective cell line is indicated.

FIG. 2. Classification of breast cancer cell lines by gene expression profile of known kinases and phosphatases. Common gene expression changes (Cluster AXL) in weakly invasive versus highly invasive BC cell lines.

Gene expression was measured by cDNA array hybridization of RNA (duplicate preparations) from each of the indicated cell lines, as described in "Materials and Methods." The 22 selected genes were differentially expressed in at least 75% of the weakly invasive BC cell lines, the highly invasive BC cell lines (red and green bar, subsequently), or both with median fold-changes of greater than 2-fold. The level of gene expression relative to MCF10A is shown by the colour and shade designated in the key at the bottom of the cluster. Each colour shade encompasses all of the values in the range spanned by the numbers beneath the scale. GenBank accession numbers (see Table 3) and descriptions for each gene, as well as the spot location on self-made arrays membranes are also provided (see separate Table 2 and 3 of genes). Confirmation studies were performed by Northern (AXL and GAS6) or RT-PCR analysis (Roche system for HER2 expression and amplification, not shown) using the same RNA preparations as in the array. Unless otherwise noted, agreement between the arrays and other methods was within 2-fold, correlative for the majority of samples; qualitative agreement with array underestimating fold-change by other methodology by at least 10-fold. The position of invasive and weakly invasive cell lines were indicated by colour bars, subsequently.

Figure 3A:
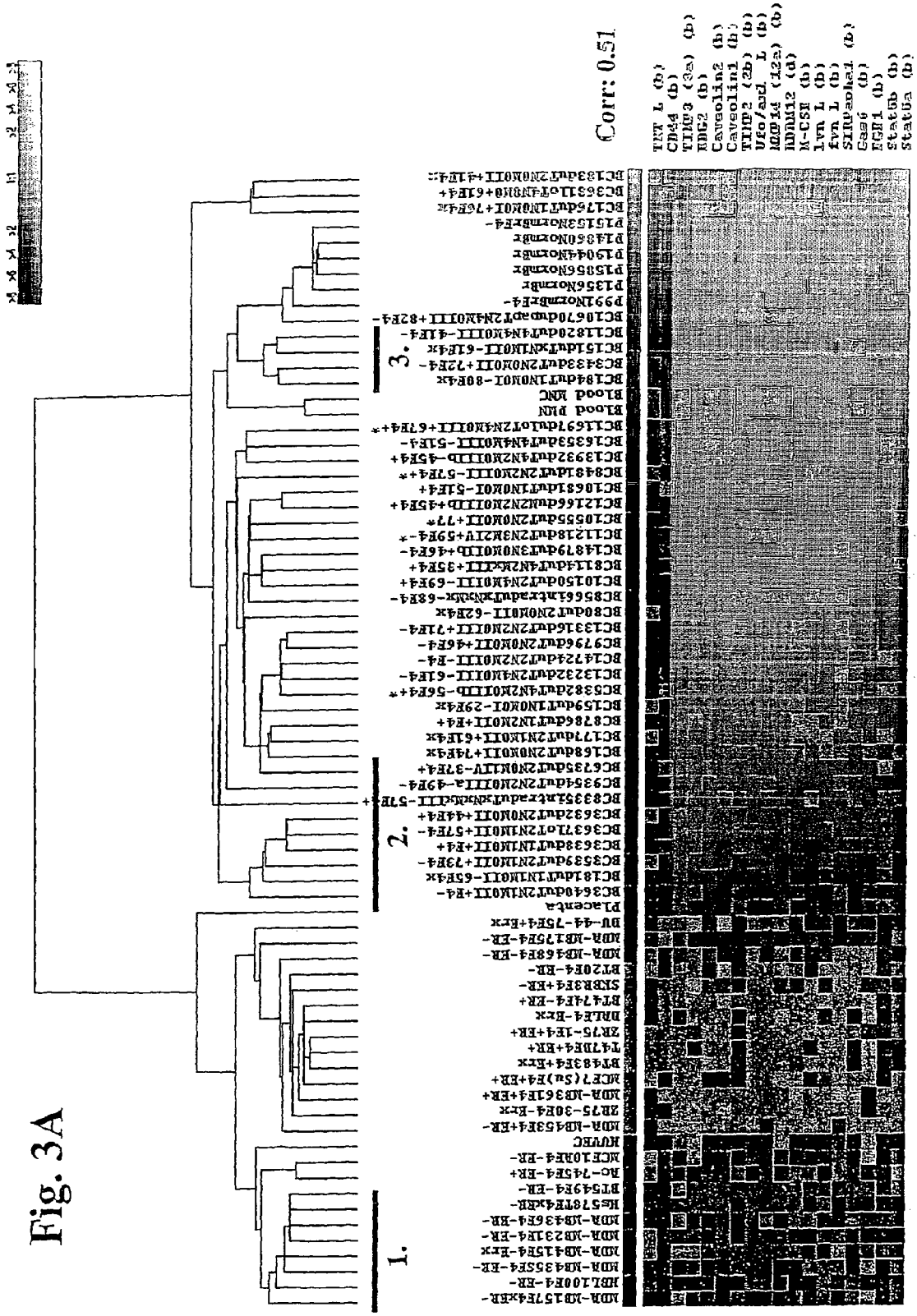

FIG. 3A, B. Classification of primary breast cancer and their cell lines by gene expression profile of the known kinases and phosphatases.

Gene expression was measured by cDNA array hybridization of RNA (duplicate preparations) from each of the indicated cell lines and primary tumors, as described in "Materials and Methods." The 26 selected genes were differentially expressed in at least 75% of the weakly invasive BC cell lines, the highly invasive BC cell lines (red and green bar, subsequently), or both with median fold-changes of greater than 2-fold. The level of gene expression relative to normal breast tissues (mix of two) is shown by the colour and shade designated in the key at the bottom of the cluster. Each colour shade encompasses all of the values in the range spanned by the numbers beneath the scale. GenBank accession numbers (see Table 3) and descriptions for each gene, as well as the spot location on self-made arrays membranes are also provided. Confirmation studies were performed by Northern (AXL and GAS6, not shown for primary tumors) or RT-PCR analysis (Roche system only for HER2 expression and amplification, not shown) using the same RNA preparations used in the array. Unless otherwise noted, agreement between the arrays and other methods was within 2-fold, correlative for the majority of samples; qualitative agreement with array underestimating fold-change by other methodology by at least 10-fold.

A. Not supervised array analysis of the normal breast tissues, primary tumors, normal breast and cancer cell lines. AXL cluster is included 18 genes (the correlation of expression is 0.51 or significant) the most of these genes were identified in breast cancer cell lines (see FIG. 2).

B. Classification primary tumors and breast cancer cell lines using only consensus invasiveness genes. All primary tumors and BC cell lines were applied for cluster analysis using 26 genes (belongs to the AXL cluster). Primary tumors and BC cell lines were recognised and most highly invasive (HI) BC cell lines belong to the same tree (with the exception of MDA-MB-231 and one primary tumor BC151, indicated by red bar).

Figure 4:
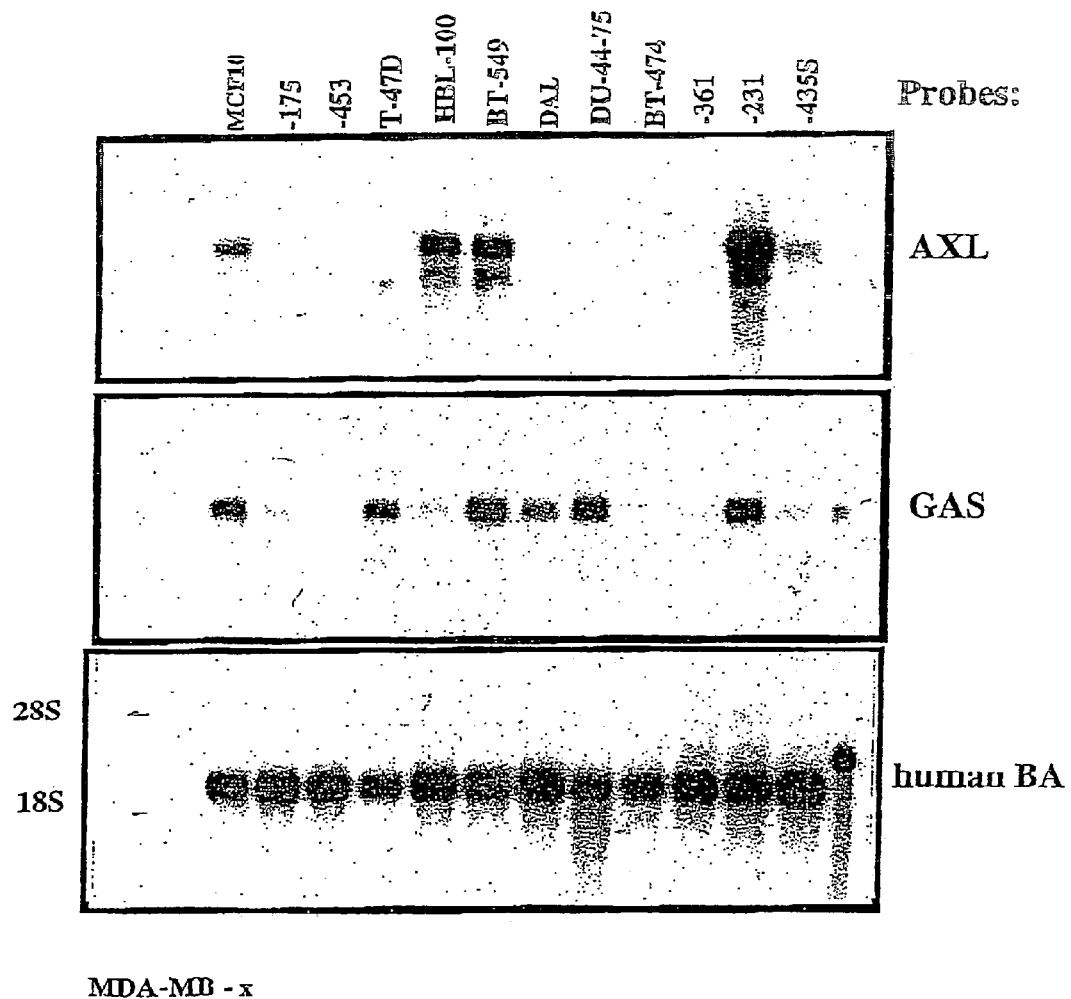

FIG. 4. Northern blot analyses of selected differentially expressed AXL/GAS genes.

mRNA (15 µg/lane) isolated from each of the indicated cell lines was analyzed for expression of the designated genes by hybridization with probes corresponding to the fragments deposited on the cDNA arrays. Expression levels for each mRNA relative to Ac745 (normal breast epithelial cells) are recorded beneath each band. The sizes (at right) corresponding to the major specific bands agree with those reported in the literature for each mRNA. The same filters were used probed and re-probed for these analyses. Panel A—expression AXL, B—GAS and C—β-actin mRNA. The levels of β-actin are shown for a representative filter as a control for equivalent sample load. mRNA was prepared from two independently grown cell cultures and tested for expression levels of the indicated genes.

FIGS. 5A and B. Morphology of BC cell lines MDA-MB-435S, BT549 and MDA-MB-231 (mock) or stably expressing dnAXL when cultured on Matrigel.

Cells were cultured on top of a Matrigel layer for 7-14 days.

A, photographs representing the three basic morphologies are shown for the indicated BC cell lines. B, Wound assays are shown for the MDA-MB-435S mock and dnAXL mutant clone 2. The position and treatment are indicated on the FIG. Magnification was ×100.

Figure 6A:
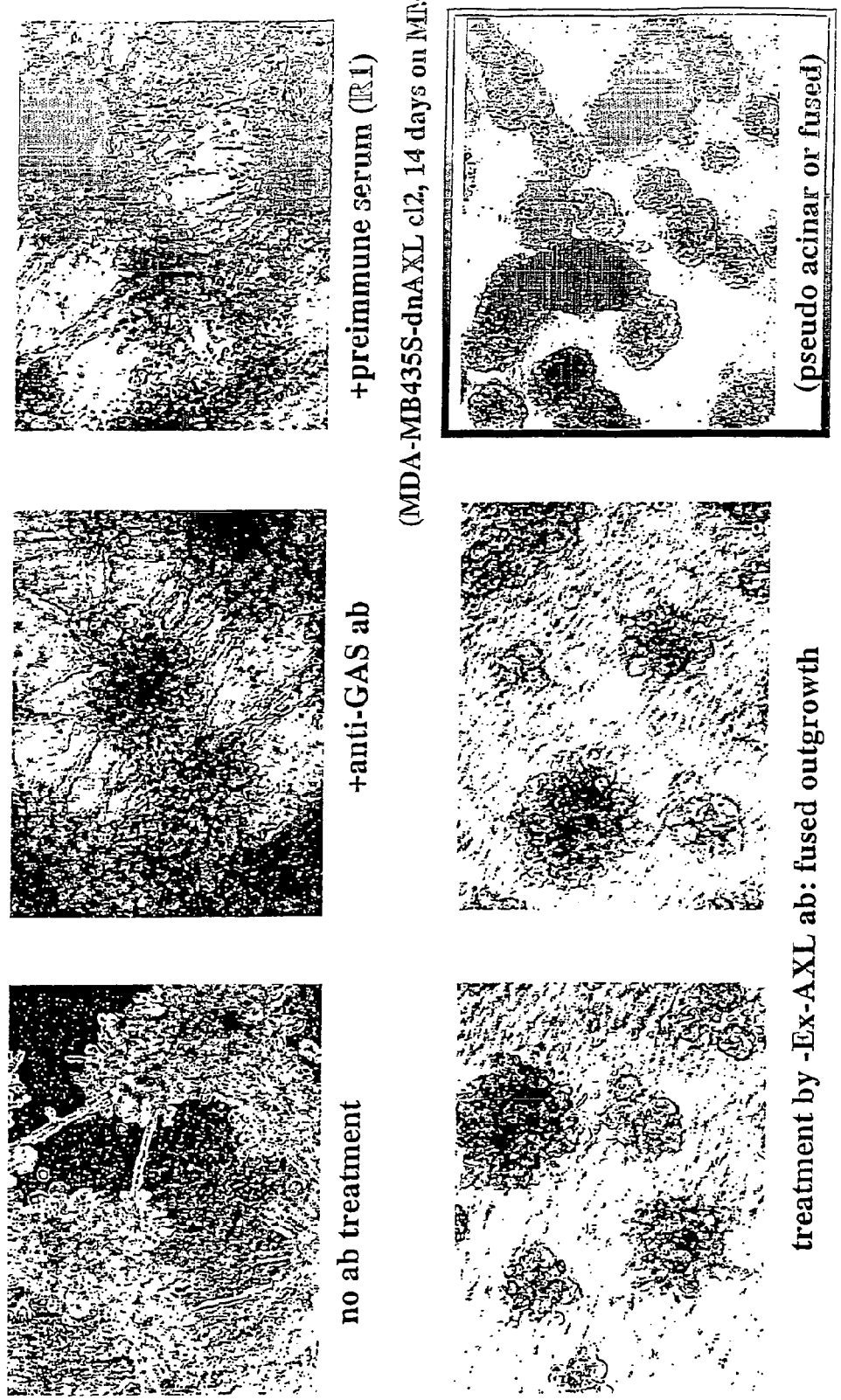

FIGS. 6A, B and C. 3D outgrowth, migratory and invasive behaviour of BC call line MDA-MB-435S, mock, stably expressing dnAXL or after treatment with anti-Ex-AXL antibody.

A. Cells were cultured on top of a Matrigel layer for 7-14 days (see legend to the FIG. 1). They were not treated or treated by antibody as indicated.

B. Invasive activities of the indicated BC cell line were measured in Boyden chambers by counting the number of cells that traversed the Matrigel (3-4 mg/ml)-coated filter in 20-36 h according to the procedure described in "Materials and Methods." Data are average values from at least two individual experiments containing triplicate points. Error bars.

C. Migration ability was assayed in parallel transwell chambers using filters without Matrigel under the same conditions as the invasion assay. Results shown are the averages of at least two experiments containing triplicate points (error bars). Cell migration was evaluated also in a Boyden chamber in the absence of the Matrigel barrier. As expected, cell lines MDA231, MDA435S, and BT549 were considerably more motile than the weakly invasive cell line, MCF7 (not shown).

Figure 7A:
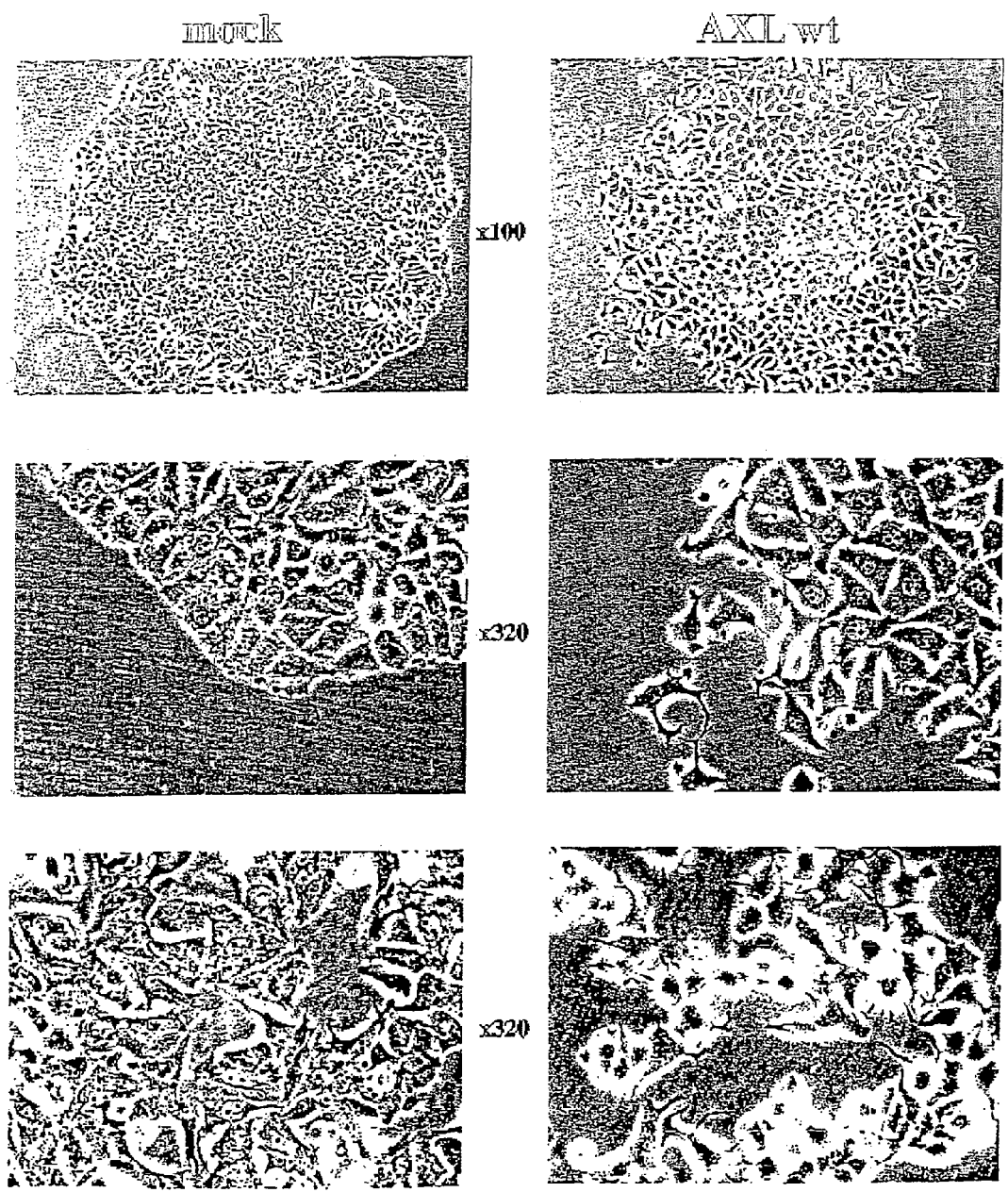
Figure 7B:
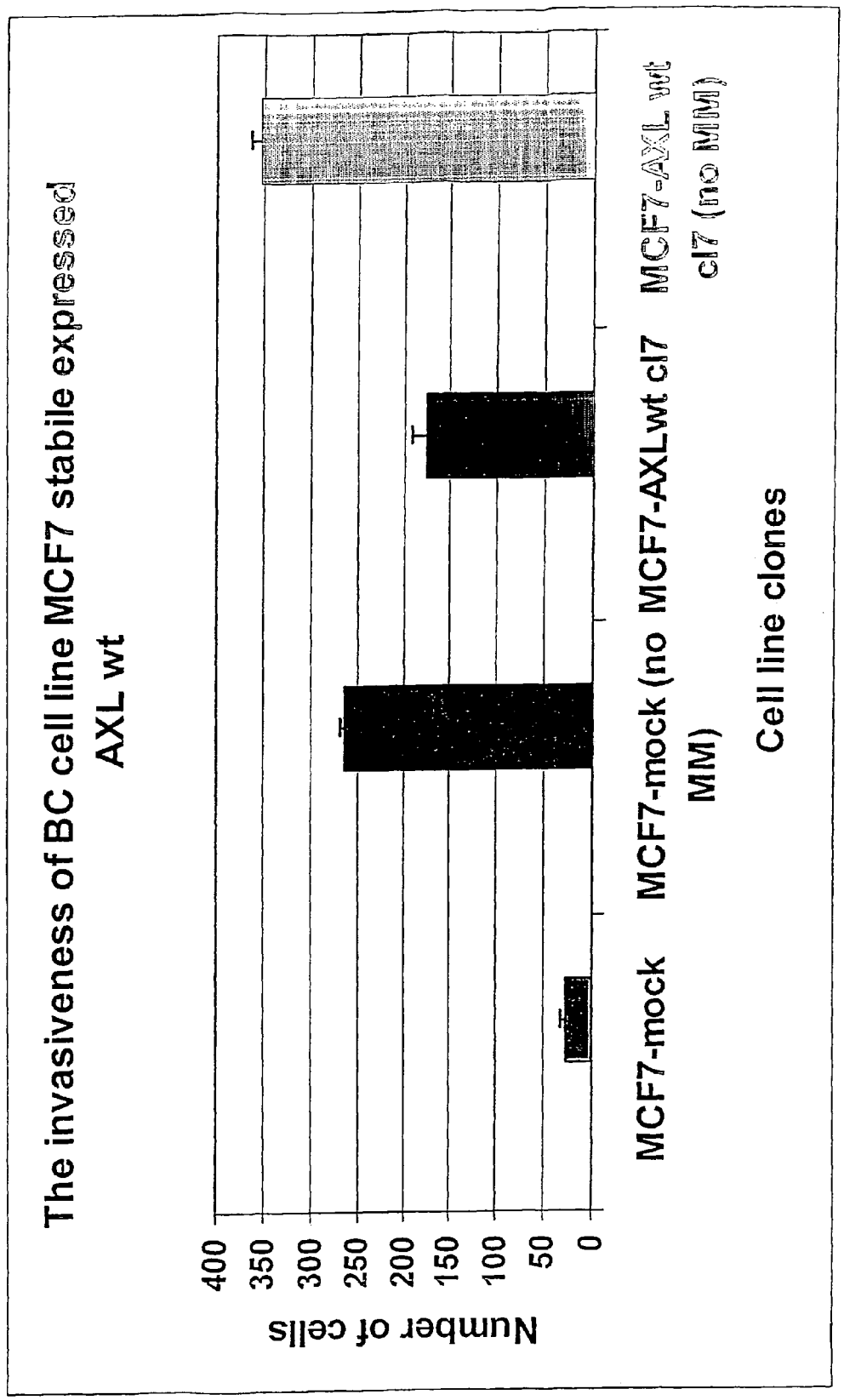

FIG. 7. Effect of AXL wt transfection on MCF7 breast cancer cells

A. The morphological effects of AXL wt infection and forced over-expression. The over-expression of AXL wt in MCF7 cells results in a change from compact cobblestone-shaped cells to irregularly shaped cells with many protruding extensions.

B. The effects of AXL wt infection on cell invasion were assayed in a Boyden chamber assay as described above (see Material and Methods). The clones MCF7-AXL wt were up to 30-fold more invasive than the empty vector-infected cells.

A total of 20,000 cells were seeded on a Boyden chamber for 36-46 h (with filters pores 8 µm, covered by matrigel matrix at concentration 3-4 mg/ml). Cells infected with AXL wt invade much sooner than cells infected with an empty vector control or dnAXL mutant form.

FIG. 8.

A. Western blot analysis of SF126 glioma cell clones expressing the control vector (SF126-mock), the wild type form of UFO/AXL (SF126-Ufo-WT), and the truncated dominant-negative mutant form of UFO/AXL (SF126-Ufo-DN). Serum-depleted cells were left untreated (−) or treated with 200 µg/ml Gas6 (+). Lysates were blotted with anti-phosphotyrosine serum (top panel) or an antibody directed against the extracellular domain of human UFO/AXL (lower row). Compared to SF126-mock cells the analyses demonstrated increased (approximately 30%) and abolished Gas6/UFO/AXL-mediated signalling in SF126-UFO-WT and SF126-UFO-DN cells, respectively. B-D. Expression of the truncated dominant-negative mutant form of UFO/AXL in SF126 cells (B) changed their morphology when compared to SF126-mock and SF126-UFO-WT cells (B and C).

FIG. 9.

A. Analysis of tumor volume for SF126 cell clones. Tumor cells were implanted subcutaneously into nude mice (n=4 animals per group) and were followed for 14 days. The mean±SEM values, are represented. * p<0.05 vs. SF126-mock cells. B. Quantitative analysis of tumor area (left panel) and functional vessel density (right panel) following implantation of SF126 cell clones into the dorsal skinfold chamber of nude mice, as assessed by intravital multi-fluorescence videomicroscopy (n=4 animals per group). The mean±SD values are represented. Statistical analysis was performed by ANOVA followed by the appropriate post hoc test for individual comparisons between groups; * p<0.05 vs. SF126-Ufo-DN cells. C and D. Representative histomorphological images of SF126-UFO-WT tumors (C) and SF126-UFO-DN tumors (D) showing differences in tumor volume. Bars indicate 1 mm. H&E staining. E and F. Representative histomorphological images of SF126-UFO-WT tumors (E) and SF126-UFO-DN tumors (F) showing differences in tumor invasion. While SF126-UFO-WT tumors massively infiltrated the adjacent skin muscle and subcutaneous tissue (E) arrows indicate remnants of destroyed muscle layer), SF126-UFO-DN tumor cell invasion was almost completely inhibited (F). Note preserved structure of muscle layer in (F). Bars indicate 100 µm. H&E staining. G and H. Fluorescence microscopy alone (G) and in combination with phase contrast (H) confirming lack of SF126-UFO-DN tumor cell invasion into adjacent tissue layers. Tumor cells were labeled with DiI prior implantation. Bars indicate 100 µm. All specimens were excised on day 21 after implantation into the dorsal skinfold chamber of nude mice. t, tumor mass; m, skin muscle layer; sc, subcutaneous tissue. SF126-mock, controls; SF126-Ufo-WT, cells expressing the wild type form of UFO/AXL; SF126-Ufo-DN, cells expressing the truncated dominant-negative mutant form of UFO/AXL.

FIG. 10.

A. MTT proliferation assay of SF126 cell clones. In abscence and presence of Gas6 (200 µg/ml). Cells were left untreated (−Gas6) or treated with 200 µg/ml Gas6 (+Gas6). Analysis was performed after 48 hours of culture. Growth rate, is expressed in relation to unstimulated SF126-mock cells. The mean values are represented. B and C. Formation of multicellular aggregates by SF126-Ufo-WT and SF126-Ufo-DN cell clones demonstrating unaltered—ability to aggregate following inhibition of UFO/AXL function. D. Migration of SF126 cell clones over an observation period of 7 days. Area of migration was analyzed planimetrically by means of an image analysis system. The mean±SD values are represented. Statistical analysis was performed by using ANOVA followed by unpaired Student's t-test. * p<0.05 vs. SF126-mock. E and F. Analysis of tumor cell invasion by 48 hour confrontation of SF126-UFO-WT tumor cell spheroids (E) or SF126-UFO-DN tumor cell spheroids (F) with fetal rat brain cell aggregates. Clear-cut border between SF126-UFO-DN tumor cell spheroid and brain cell aggregate indicates lack of invasiveness following inhibition of UFO/AXL function. B, brain cell aggregate; S, tumor spheroid. SF126-mock, controls; SF126-Ufo-WT, cells expressing the wild type form of UFO/AXL; SF126-Ufo-DN, cells expressing the truncated dominant-negative mutant form of UFO/AXL.

FIG. 11.

A. Survival curve for adult nude mice following stereotactic implantation of SF126-Ufo-WT cells and SF126-Ufo-DN cells into the brain (n=4 animals per group). Animals were sacrificed as soon as they developed neurological deficits or lost >30% of their initial body weight. B-E. Histomorphology of SF126-Ufo-WT tumors after implantation into the brain showing diffuse tumor cell infiltration into adjacent brain tissue (B). Tumor cells infiltrated via the perivascular space (C), along white matter tracts (D), and along the wall of the ventricular system (E). H&E staining. Bars indicate 100 µm.

EXAMPLES

A. Breast and Prostate Cancer Studies
1. Materials and Methods
1.1. Tumor Samples and Cell Lines To avoid any bias of selection as to the type and size of breast cancer (BC) and others tumors, the RNAs to be tested were prepared from unselected samples. Samples of primary invasive breast carcinomas were collected from 72 patients undergoing surgery. After surgical resection, the tumors were macrodissected: a section was taken for the pathologist's diagnosis and an adjacent piece was quickly frozen in liquid nitrogen for mRNA extractions. The median age of patients at the time diagnosis was 55 years (range 29-81) and most of them were postmenopausal. Tumors were classified according to the WHO histological typing of breast tumors: ductal carcinomas, lobular carcinomas, mixed ductal-lobular carcinomas and medullary carcinomas. Pooled "normal" cDNA derived from normal breast mRNAs (3) was used as control and for normalisation. Expression profiles of protein kinases (PK) and phosphatases (PP) in "normal" cDNAs mentioned above were evaluated separately. In this study we also included 21 BC and 3 normal breast epithelial cell lines. The sources of the breast cancer cell lines were as follows: BT-20, BT-474, BT-483, BT-459, Du-4475, MDA-MB-134, -157, -175, -361, -436, -453, -468, SK-BR-3, and ZR-75-1, T-47D, MDA-MB-231, ZR-75-30 were obtained from the American Type Culture Collection (ATCC, Rockville, Md.). MCF-7, clone and BC cell line DAL were supplied by SUGEN (Redwood City, Calif.). The HBL-100 cell line was from ATCC. This cell line was derived from normal tissue but contains tandemly integrated SV-40 sequences (9). Cultures were maintained in exponential growth in RPMI 1640 medium, supplemented with 6 mM glutamine, 10 µg/ml human insulin and 10% Fetal calf serum (FCS) (CSL, Parkville, Australia). Normal breast epithelial cell strains MCF10A, MCF10 T-24 and MCF10 neo were provided by Dr. B. Gilles (Arizona Cancer center). Ac745 was provided by Dr. M. Stampfer and grown in the DMEM F12 medium supplemented by the condition medium of Hs578Bst, Insulin, Hydrocortisone, EGF, Cholera toxin, vitamins and antibiotics.

Cells were free from Mycoplasma contamination.

1.2. Isolation and Fractionation of RNA and DNA.

Total RNA and genomic DNA was isolated from the same cell pellet by lysis in guanidinium isothiocyanate solution (GTS buffer: 4 M guanidinium isothiocyanate, 25 mM sodium citrate pH 7.0, 0.5% Sarkosyl, and 0.1 M β-mercaptoethanol) followed by phenol-chloroform extractions. Total RNA was isolated using standard methods (Sambrook et al. [1989]) with modifications. DNA was collected and extracted twice with an equal volume of phenol:chloroform:isoamylalcohol (25:24:1). RNA and DNA were isolated from each cell line on a minimum of 3 independent occasions.

Total and mRNA integrity and cDNA complexity was controlled by agarose gel electrophoresis and Northern blots using specific probes. Some mRNA extraction was performed using the OligoTex mRNA isolation Kit (Quiagen Biotech, Germany). Cell pellets were resuspended in lysis/binding buffer, vortex-mixed briefly, passed three times through a 21 G needle and applied to a spin lysate column and centrifuged at 13,000 g for 3 min. The lysate was then mixed gently with Oligo-dT cellulose (Stratagene Inc.) and applied to a pre-wetted Oligotex molecular biology column (Quagen Biotech). The column was washed three times with lysis/binding buffer and four times with wash buffer before eluting the mRNA with pre-warmed (65 C) elution buffer. The quantity of mRNA was measured using the OD260.

1.3. cDNA Arrays Preparations

PK and PP gene expression was analyzed by hybridization on nylon filters arrays with radioactive targets (cDNA). The arrays contained 645 genes encoding kinases, phosphatases and others signaling proteins: ligands, adaptors, transcription factors, metalloproteinases/ADAMs, apoptosis related genes and 11 house keeping genes (the list is available at [[http://]] www.biochem.mpg.de or ullrich@biochem.mpg.de). Their identity was verified by sequencing of plasmid DNA and compared with GenBank sequence information. Identity of PK and PP was conformed for all clones spotted on nylon filters ones, or in duplicate. For normalization purpose, the FGP gene was spotted two times as well as genomic and vector DNA. Purification of plasmids was done using a plasmid purification kit (Qiagen, Germany).

1.4. cDNA Array Hybridization

Filters were initially pre-washed in 0.5% SDS for 5 min, with agitation. In 10 ml of the pre-hybridisation solution was included Yeast tRNA. Human Cot-1 DNA (BRL/Life technologies) was used in the hybridization step which was performed in a Roller bottle (Hybaid Inc.) for 16 h in a roller oven at 65° C. Labelled probe was denatured for 10 min at 100° C. and then placed immediately into the hybridisation mixture which was incubated for a further 18 h at 65° C. After 18 h, the hybridisation mixture was discarded and the array was washed twice in 2 sodium chloride: sodium citrate (SSC) buffer, 0.2% SDS for 20 min at 42° C. with continued rotation in the incubator. A third wash was performed in 0.2×SSC, 0.1% SDS for 15-60 min at 65° C. in a plastic box with horizontal shaking. After the third wash, the filter was placed on a piece of moistened Whatman paper and covered with Saran wrap. The array was then placed into an imager cassette with a Phosphorimager storage screen (Fuji, Japan) and exposed for 2 days.

1.5. Image Acquisition and Analysis

Exposed phospho-imager storage screens were scanned once on a Phosphoimager Scanner (Fuji) at a resolution of 50 microns and were visualised using MacBAS 2000 (Fuji). Images were imported into Array Vision V(Canada) for analysis by a software protocol. Mapping of individual elements to an internal reference database was achieved by aligning the images onto a software-based matrix using a total of 4 control elements representing total genomic control DNA, GFP, and vector. Normalisation was performed by multiplying the raw intensity for each data element by a normalisation factor equal to the average raw intensity for all the vector elements divided by 100 (this value is the average raw intensity for all elements, derived from a large number of different hybridizations performed by us the development of the arrays). Software-based pair-wise comparisons of the normalised images were made against the image obtained from hybridisation of labelled cDNA taken from pooled "normal" cDNA derived, from normal breast RNAs, immortal (preneoplastic) breast epithelial cell lines, as indicated above. Changes in expression levels were calculated using normalised intensities and given as ratios (positive ratios indicated an increase in transcript levels, negative ratios indicated a decrease in transcript levels) and were visualised by Scatterblot graphics and TreeView program (13-16).

1.6. Array Data Analysis

Before analysis of the results, the reproducibility of the experiments was verified by comparing duplicate spots or one hybridizations with the same cDNA on two independent arrays, or two independent hybridizations with cDNA prepared from the same RNA. In each case, the results showed good reproducibility with respective correlation coefficients 0.96, 0.98 and 0.98 (data not shown). The reproducibility was sufficient enough to consider a 2-fold expression difference as significantly differential. Subsequent analysis was done using Excel and statistical software. The search for genes with expression levels correlated with tumor parameters was done in several successive steps. First, genes were detected by comparing their median expression level in the two subgroups of tumors differing according to parameters of interest. We used the median values rather than the mean values because of the high variability of the expression levels for many genes, resulting in a standard deviation expression level similar or superior to the mean value and making comparisons with means impossible. Second, these detected genes were inspected visually on graphics and, finally, an appropriate statistical analysis was applied to those that were convincing to validate the correlation. Comparison of HER2 expression between ER-positive tumors and ER-negative tumors was validated using a Mann-Witney test. Correlation coefficients were used to compare the gene expression levels with the number of axillary nodes involved.

1.7. Cluster Analysis

The data from this study were analyzed and displayed as described (13-16). Briefly, a hierarchical clustering algorithm produces a table of results wherein the elements/cDNAs of the array (representing specific genes) are grouped together based an similarities in their patterns of gene expression.

The same algorithm is applied to cluster the experimental samples (i.e., cell lines and tumors) according to the similarities in their overall patterns of gene expression. The data tables, thus ordered, are presented graphically as colored images. Along the vertical axis, the genes analyzed are arranged as ordered by the clustering algorithm, so that the genes with the most similar patterns of expression are placed adjacent to each other. Along the horizontal axis, experimental samples are similarly arranged such that those with the most similar patterns of expression across all genes are placed adjacent to each other. The colour of each cell/square in this tabular image represents the measured expression ratio of each gene in question. The colour saturation is also directly proportional to the magnitude of the measured gene expression ratio with the brightest red squares having the highest T/N ratio (i.e., >8-fold difference), the brightest green squares having the lowest T/N ratio, black squares indicating a ratio of approximately 1, and grey squares indicating insufficient data quality.

1.8. RNA Analysis by Northern-Blot

We used standard protocol of Northern-blot analysis for detection of the expression AXL and GAS6 genes in preparation of some breast cancers and all breast cancer cell lines. The loading RNA samples were verified by re-hybridization of filters with a human β-actin probe.

1.9. Chemoinvasion and Migration Assays

The chemoinvasion assay was carried out using a modification of the method of Albini et al. (10). After trypsinization, cells (20.000) were plated on Matrigel-coated (150 μl of 4.0 mg/ml) 8-μm polypropylene filter inserts in Boyden chambers (Biocoat Matrigel Invasion Chamber, Becton Dickinson, Bedford, Mass. or Nunc 10 mm tissue culture inserts, Naperville, Ill.). The bottom chamber contained 0.55 ml of NIH3T3-conditioned media, produced as described by Albini et al. or normal growth media for some cell lines.

BC cell lines obtained from the ATCC were trypsinized, centrifuged, and resuspended at $4 \times 10^5$ cells/ml in RPMI medium containing 10% FBS. The remaining cell lines were resuspended in the irregular growth medium.

After 20-36 h, the cells remaining in the insert were removed with a cotton swab, and the cells on the bottom of the filter were counted using different protocols: fixed in Diffquick (American Scientific Products, McGraw Park, Ill.) and treated with RNase A (at 50 μg/ml for 20 min at 37° C.) before staining with propidium iodide (10 μg/ml in PBS) for 1 min at room temperature (RT). The dried filters were removed and mounted on slides with Cytoseal 60 mounting media (Stephens Scientific, Kalamazoo, Mich.). Individual propidium iodide-stained nuclei on the filters were counted. Most results were obtained using trypsinization and counting of the cells. Triplicate samples were counted in each experiment. Outlying values were eliminated from calculations of average invasive activity.

For invasion assays in presence of antibody, cells were seeded on Matrigel and, when attached, the indicated antibody was added to the medium. The antibody was present in the upper chamber for the entire duration of the assay; at the end of the assay cell viability in the upper chamber was assessed by Trypan blue. Migration activity was determined following the procedure described for the invasion assay except that the cells were plated on top of uncoated 8-μm pore polypropylene filters in the Boyden chambers.

1.10. Matrigel Outgrowth

Determination of the morphology of cells grown on Matrigel was carried out as described previously (10). Briefly, cells (5000 cells/well of a 96-well plate) resuspended in 50 μl of culture medium were plated on top of a pre-set Matrigel coating consisting of 70 μl of Matrigel (Becton Dickinson) diluted to 6.0 mg/ml in -RPMI basal medium salts. After polymerization on the top of these diluted 50 μl of Matrigel (1.0 mg/ml) were added. Colony outgrowth was monitored over the course of the experiment and photographed at 7-14 days using a Zeiss AxioVert 35 microscope equipped with a OpenLab (UK) digital camera.

1.11. Wound Assay

After overnight starvation, wounds were made on confluent cell monolayers with a plastic tip. MDA-MB-345S-mock and MDA-MB-435-dnAXL, clone 2 cells were treated with culture medium (10% FCS) and culture medium containing GAS6 (200 ng/ml) for 12, 24 and 48 h, before taking pictures (phase contrast). To quantify cell migration, three randomly chosen regions of a wound (1 mm long) were photographed at a magnification of 40×; a mean wound width was measured every 20 μm, and an average percent wound closure was calculated. Three independent wounds were examined per sample and a mean percent wound closure was calculated.

1.12. The Treatment of Cells with Antibody

Breast cancer cells (5000 for the 3D outgrowth assay and 20000 for the invasion assay in a Boyden chamber) were treated by Ex-AXL polyclonal antibody (200 μg/ml) using 50 μl of antibody and 500 μl cell suspension. Cells were incubated with antibody 60 min at RT and then washed in PBS at RT. Plating of cells and the following 24 h treatment interval were performed with the same concentration of Ex-AXL antibody.

1.13. Infection of BC Cells with Recombinant Retroviruses

AXLwt and dn-AXL mutant forms of the viruses were obtained according to a standard protocol (31) with modifications. Briefly, pLXSN-AXLwt and pLXSN-dnAXL were cloned via EcoRI/BamHI and NotI/XbaI sites, subsequently.

The packaging cell line Phoenix A was transfected with these vectors using calcium phosphate. The supernatant of transfected Phoenix A cells was collected and filtered trough a 0.45-μm filter for the infection of the human cancer cell line, cells were incubated with viral supernatant for 24 h. After 48 h, medium was replaced with medium containing 400 μg/ml G148. For further selection, cells were incubated with G418 for 14 days. Polyclonal and monoclonal cell lines were generated by limited dilution. AXL expression was monitored by Western blot and array analysis. Polyclonal and three monoclonal cell lines with similar expression levels of AXL wt and dn-AXL were chosen for further experiments.

1.14. Antibodies

AXL/UFO-specific antibodies were generated by immunization of rabbits with recombinant GST-AXL extra-cellular domain fusion protein containing amino acid residues 1-410 (AXL-Ex). The recombinant GST-AXL-Ex protein was stably secreted by transfected HEK293 cells (vector pcDNA3-GST). Culture medium was collected and GST-AXL-Ex protein purified using standard GST-tag protocol (Pharmacia, Sweden). AXL-Ex polyclonal antibodies were partially purified on GST-Sepharose affinity columns.

2. Results

The purpose of this study was to establish expression profiles of protein kinase, phosphatase and signalling genes in breast cancer cells with the objective of identifying novel markers for breast cancer aggressiveness. cDNA hybridization arrays were used to analyze the gene expression profiles of 14 weakly, 7 highly invasive breast cancer cell lines and 3 normal breast epithelial cell lines (Table 1, FIG. 1, 3D growth of invasive BC cell lines and control).

28-30) and Table 2). Other genes of the cluster were identified for the first time as genes associated with cancer cells aggressiveness: AXL, GAS, MMP14, Adam12, Adam17, MT3MMP, FGF2 and 5, Fyn, Lyn, DDR2, TIMP1, HB-EGF, SGK, S6KII, MAP4K4, SIRPα and Annexin 2.

Figure 3B:
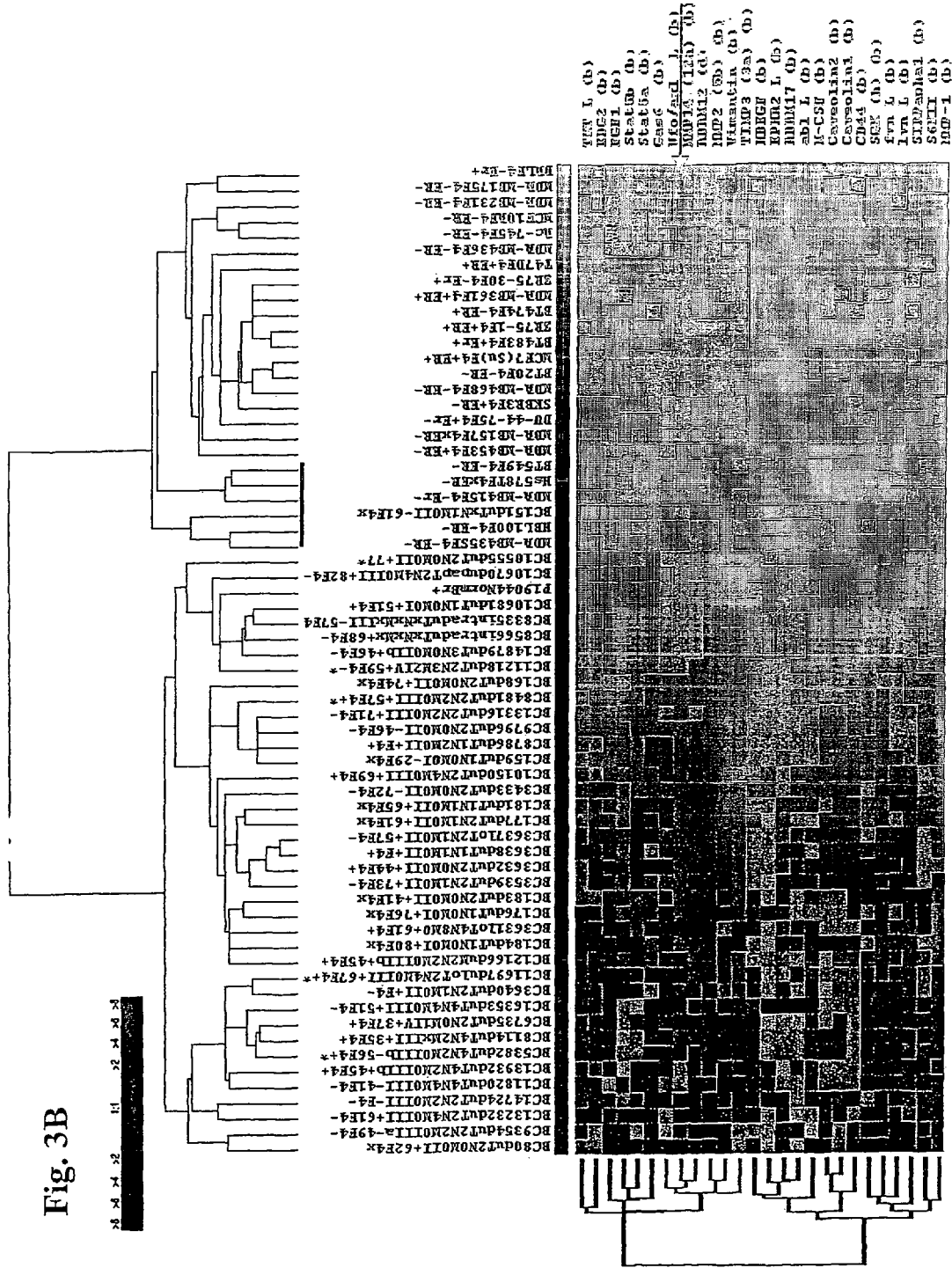

Remarkably, no one of these BC cell lines did express estrogen receptor (see FIG. 3, as indicated for the BC cell lines characteristics). Cluster AXL of the co-expressed genes was identified in primary BC (FIG. 3) and others tumors and

TABLE 1

Characteristics of the breast cancer cell lines used to generate the consensus of invasiveness

| Cell line | Specimen origin a | Tumorigenicity b | Matrigel morphology c | Marker gene expression d | | |
|---|---|---|---|---|---|---|
| | | | | ER- | E-cad | Vim |
| Weakly invasive | | | | | | |
| ZR-75-1 | Infiltrating ductal Ca; PE | +e | Fused | + | + | − |
| T47D | | | | | | |
| ZR75-1 | Infiltrating ductal Ca; ascites | +e | Fused | + | + | − |
| MCF7 | Breast adenocarcinoma; PE | +e | Fused | + | + | − |
| MDA361 | Breast adenocarcinoma; brain met | +e | Fused | + | + | − |
| BT474 | Invasive ductal Ca; PT | +e | Fused | + | + | − |
| BT20 | Breast adenocarcinoma: PT | + | Fused | − | ND | − |
| MDA468 | Metastatic adenocarcinoma; PE | + | Fused | − | − | − |
| SKBR3 | Breast adenocarcinoma; PE | + | Spherical | − | − | − |
| MDA453 | Metastatic breast Ca; PE | − | Spherical | − | − | − |
| BT483 | | | | | | |
| MDA175 | | | | | | |
| Du44-75 | | | | | | |
| DAL | | | | | | |
| ZR-75-30 | | | | | | |
| HBL-100 | | | | | | |
| Highly invasive | | | | | | |
| MDA435S | Metastatic ductal adenocarcinoma | +, met | Stellate | − | − | + |
| BT549 | Papillary invasive ductal Ca; PT | − | Stellate | − | − | + |
| Hs578T | Ductal Ca; PT | +, met | Stellate | − | − | + |
| MDA231 | Breast adenocarcinoma: PE | +, met | Stellate | − | − | + |
| MDA436 | in progress | | Stellate | | | |
| MDA415 | in progress | | | | | |
| MDA157 | in progress | | Stellate | | | |

Remarks:

a) Specimen origin and pathological assessment information were obtained from the ATCC catalogue. PT, primary tumor; PE, pleural effusion; Ca, carcinoma.

b) Tumorigenicity data was reported in the ATCC catalogue or in Ref. 17. +, palpable tumors produced as xenografts in athymic nude or SCID mice; −, nontumorigenic; met, metastatic cell lines as reported by Refs. 18 and 19.

c) Description of the morphology of cells cultured in Matrigel and their activity in the Boyden chamber invasion assay was taken from Ref. 10.

cDNA microarray membranes, containing 650 genes were used in these studies. Differences in gene expression between weakly and highly invasive BC cells were identified that enabled the definition of "consensus of invasiveness" for each invasive phenotype (FIG. 2, Cluster AXL, correlation >0.71). Highly invasive BC cell lines (BT549, MDA-MB-231, MDA-MB-436, MDA-MB-415, Hs578T, MDA-MB-157 and MDA-MB-435S) over-expressed AXL and show a defined gene express ion profile that discriminate them from weakly invasive BC cell lines and "normal" breast epithelial cells. These bluster included genes already known as markers of invasiveness (CD44, VIM, CAV1, 2 and MMPs (Ref. 20-27)). Some of these genes have only been considered for association with cancer cell invasiveness (M-CSF and EPHA2 (Ref.

cancer cell lines (kidney, prostate and glioblastomas) as well (data not shown). The expression of the AXL and GAS genes in invasive BC cell lines were conformed by Northern-blot hybridization (FIG. 4).

The dominant negative mutant of the AXL gene (dnAXL) which was stable over-expressed in highly invasive BC cell lines strongly suppressed invasiveness, migration and survival of, the several BC cell lines: MDA-MB-435S, BT549, and partially MDA-MB-231 (FIGS. 5A and B). All clones having stable dn-AXL expression had 3D-growth on the Matrigel matrix like non-invasive or weakly invasive breast cancer cell lines, for example, MCF7. The dn-AXL expression significantly inhibits GAS6 signalling and results in reduced or lacking AXL phosphorylation upon GAS treatment. ERK2 signalling in these cells was also blocked.

Figure 6B:
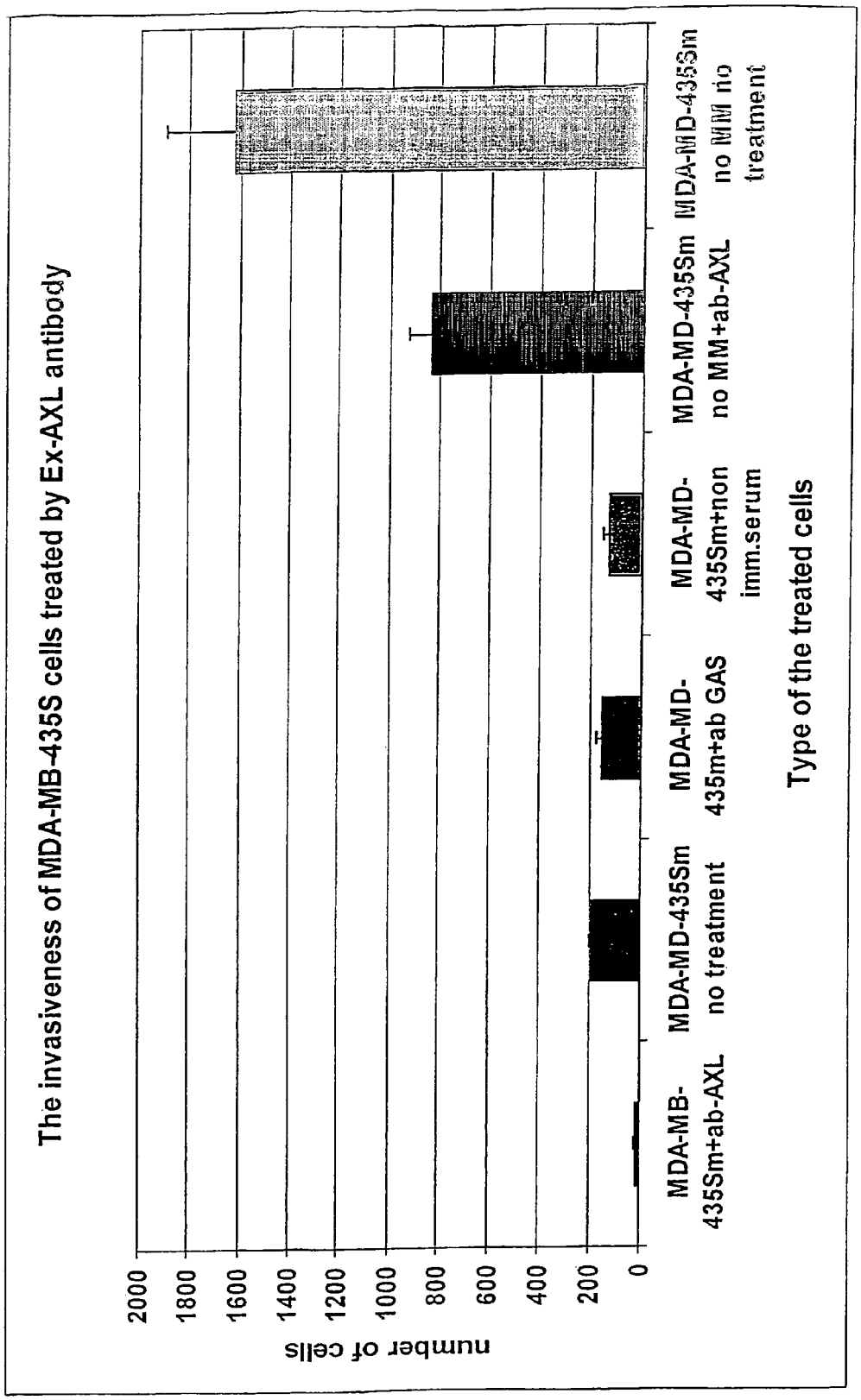
Figure 6C:
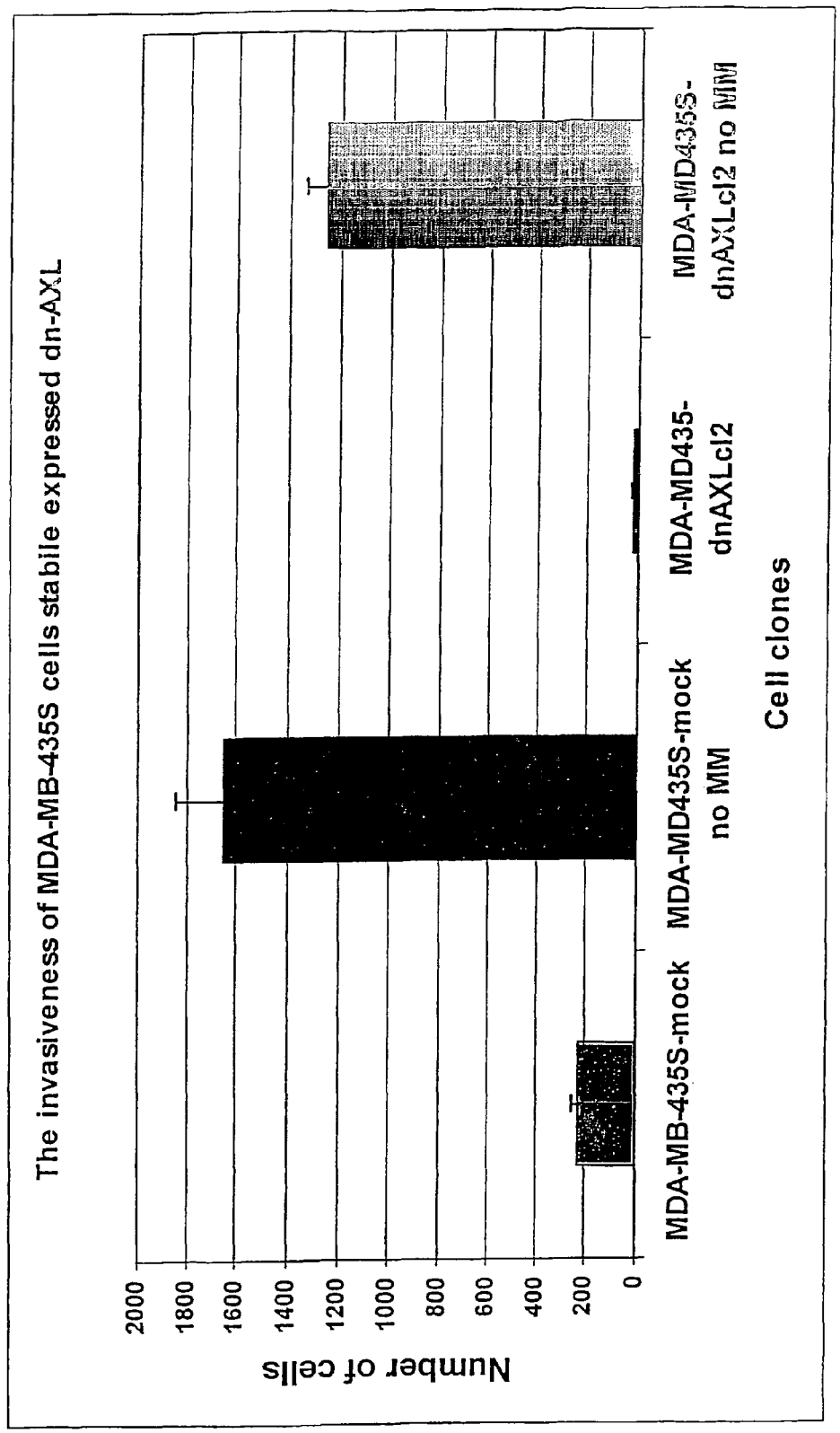

A polyclonal antibody directed against extracellular portion of AXL (containing amino acids residues 1-410, Ex-AXL) alters the cell morphology (FIG. 6A) and has very strong inhibitory activity on the migration and invasion of the MDA-MB-435S and BT549 BC cell lines (FIGS. 6B and C). Similar results were obtained with the prostate cancer cell line PPC1. Moreover, over-expression of wild-type (wt) AXL in the weakly invasive BC cell line MCF7 and prostate cancer cell line LNCaP resulted in a transformation in to a highly invasive phenotype.

B. Glioblastomas Studies

1. Material and Methods

1.1 Human Glioma Cells

The following human glioma cell lines were used in this study: U-118, U-1242, SF126, A-172, U-373, U-1240, T-98G, SF763, and SF767. All cells were grown in 10% fetal bovine serum (PAA GmbH, Linz, Austria) at 37° C. in 5% $CO_2$ humidified incubators and tested routinely for Mycoplasma contamination with Hoechst 33258 stain. Growth media (all from Gibco, Karlsruhe, Germany) were used as follows: DMEM for U-118, T-98G, and SF763; MEM, nonessential amino acids (1:100 dilution of stock; Gibco), 1 mM Na-Pyruvate for U-1242; DMEM with 4.5 g/L Glucose for SF-126, A-172, and U373 and MEM for U-1240 and SF767. Prior to tumor implantation into the dorsal skinfold chamber preparation, cells were stained with DiI as previously described (Reference 35).

1.2 cDNA Array Hybridization

The content of the cDNA array as well as its hybridization technique have been previously described in detail (Reference 31). The array comprised 125 cDNA fragments, corresponding to 84 RTKs and 30 protein tyrosine phophatases, plus control cDNAs. Total RNA, Poly(A)+RNA, and cDNA probes were generated as described elsewhere (Reference 31). Labeling of 3-5 µl of cDNA was performed with the Megaprime kit (Amersham) in the presence of 50 µCi of [$^{32}$-P]dATP. The prehybridization solution was replaced by the hybridization solution containing 5×SSC, 0.5% (v/v) SDS, 100 µg/ml baker yeast tRNA (Roche), and the labeled cDNA probe (2-5×106 cpm/ml) and incubated at 68° C. for 16 h. Membranes were washed under stringent conditions. A phosphorimager system (Fuji BAS 1000; Fuji) was used to quantify the hybridization signals. Average values for each slot were calculated using the formula: A=(AB−B)×100/B; [A, final volume; AB, intensity of each slot signal (pixel/$mm^2$); B, background (pixel/$mm^2$)]. Results of the cDNA array had to be confirmed by RT-PCR analysis as previously described (Reference 31).

1.3 Generation of Expression Constructs and Stable Cell Lines.

The 2.7 kbp cDNA sequences coding for AXL were cloned into the EcoRI/BamHI restriction sites of the retroviral vector pLXSN. The dominant-negative variant was generated by subcloning the 1.5 kbp EcoRI/FspI fragment into the same vector. Expression plasmids and empty vector were transfected into Phoenix-Ampho cells using a calcium phosphate coprecipitation method. Supernatants containing recombinant retroviruses were harvested 28 h after transfection, mixed with polybrene at a final concentration of 8 µg/ml, and applied for 3 h to subconfluent SF126 cells. Infection was repeated twice with fresh supernatant of the same producer cells. Infected cells were passaged after one day and selected with 1 mg/ml G418 for two weeks. Monoclonal cell lines were selected for high expression of AXL as monitored by western blot analysis.

1.4 Immunoprecipitation and Western Blotting

Cells were lysed in 50 mM Hepes pH 7.5, 150 mM NaCl, 1 mM EDTA, 10% glycerol, 1% Triton X-100, 10 mM $Na_4P_2O_7$ supplemented with 10 µg/ml Aprotinin, 1 mM PMSF, 2 mM $Na_3VO_4$, 10 mM NaF. Protein concentrations were determined by the micro BCA protein assay (PIERCE, Rockford, Ill.). AXL was precipitated from 1.8 mg of total cellular proteins using 30 µl of protein A sepharose suspension (CL-4B, Amersham Biosciences, Freiburg, Germany) and 3 µl anti-AXL polyclonal rabbit serum (Reference 36) overnight at 4° C. Precipitates were washed three times with HNTG buffer (20 mM. Hepes pH 7.5, 150 mM NaCl, 10% glycerol, 0.1% Triton X-100). Immunoprecipitates or 200 µg of total cellular proteins per lane were mixed with reducing sample buffer, separated by 7.5% SDS-PAGE, and transferred to nitrocellulose: membranes (Protran; Schleicher&Schuell, Dassel, Germany). Membranes were blocked with 0.25% gelatine in 150 mM NaCl, 50 mM Tris-HCl pH 7.5, 5 mM EDTA, 0.05% Triton X-100 and incubated over night at −4° C. with anti-phosphotyrosin monoclonal antibody 4G10 diluted 1:5000 in the same buffer. Secondary antibody goat anti-mouse HRP (1:10000, BioRad) was applied for 60 min at room temperature. Membranes were stripped for 90 min at 55° C. before reprobing with anti-AXL (polyclonal rabbit serum, 1:1000) and protein A-HRP (Bio-Rad, 1:40000). Detection was performed with Western Lightning reagents (Perkin Elmer Life Sciences, Boston).

1.5 Mice

Athymic nude mice (nu/nu; male/female) were bred and maintained within a specific pathogen germ-free environment and were used at 6-10 weeks of age. Experiments were performed in accordance with, the approved institutional protocol and the guidelines of the Institutional Animal Care and Use Committee. For surgical procedures mice were anaesthetised by s.c. injection of ketamin/xylazine.

1.6 Subcutaneous and Orthotopic Xenografts

Glioma xenografts were grown subcutaneously following injection of $1 \times 10^6$ C6 cells (Reference 44) into the left flank regions of nude mice. Tumor growth was assessed using vernier calipers until day 14 after implantation. Tumor volume was calculated as (length×width×height)/2. For intracerebral tumor cell implantation the head of nude mice was fixed in a stereotactic rodent head holder. Implantation was performed by injecting $5 \times 10^5$ cells stereotaectically in the right striatum. All animals were sacrificed as soon as animals in one experimental group developed neurological deficits or lost >30% of their body weight in order to compare tumor growth.

1.7 Dorsal Skinfold Chamber Model

Two symmetrical titanium frames flanked the dorsal skinfold of animals to sandwich the extended double layer of skin and create the dorsal skinfold chamber which consist of one layer of striated muscle, subcutaneous tissue, and epidermis. An observation window, covered with a glass cover slip, allowed for repeated intravital microscopic observations of the microvasculature of the tumour growing in the chamber. Two days after chamber preparation, the coverslip of the dorsal skinfold chamber was temporarily removed for tumor cell implantation. The animals tolerated the skinfold chambers well and showed no signs of discomfort or changes in sleeping and feeding behavior.

1.8 Intravital Multi-Fluorescence Microscopy

Intravital epi-fluorescence videomicroscopy was performed over 21 days following implantation (References 37, 38, 39). DiI-labeling of glioma cells allowed for precise delineation of the tumor from the adjacent host tissue as well as identification of individual tumor cells applying green light epi-illumination (520-570 nm). Contrast enhancement with FITC-conjugated Dextran (MW=150,000; 0.1 ml i.v) and use of the blue light epi-illumination (450-490 nm) was applied to visualize individual blood vessels. Tumor growth was assessed by measurement of the tissue area covered by the fluorescently-labeled tumor mass. Analysis of the host and tumor microvasculature included the vessel density and the vascular diameter (Reference 37).

1.9 Histology

Upon completion of experiments, the glioma containing dorsal skinfold chamber preparations and brains were dissected free, and frozen in liquid nitrogen for histomorphological analysis. The sections were mounted on stubs, embedded in Tissue-Tek (Miles Laboratories Inc., Naperville, Ill.) and frozen in 2-Methylbutane (E. Merck, Darmstadt, Germany) cooled with liquid $N_2$. Serial axial sections (5 µm) were cut and mounted on slides pre-coated with gelatine (Sigma). The sections were stained with Harris Haematoxylin and Eosin G (Merck) according to standard procedures.

1.10 Proliferation Assay

Proliferation of glioma cell lines was assessed in a 3-(4,5-dimethylthiazol-2-yl)-2,5-diphenyltetrazolium bromide (MTT) assay (Boehringer Mannheim, Mannheim, Germany). Cells were seeded in 96-well tissue culture plates at a concentration of 3000 cells/well and were cultured for 48 hours either in the absence or in the presence of Gas6 (200 µg/ml). Cells were then assayed for their abilities to reduce MTT dye to a colored formazan product, as an index of cell proliferation.

1.11 Migration Assay

Glioma cell spheroids were produced by seeding $5 \times 10^6$ cells in culture medium into a 75-$cm^2$ flask previously base coated with 1.0% Noble agar (DIFCO, Detroit, Mich.). After 7-10 days in culture, spheroids with a diameter less than 300-µm were chosen for the migration and invasion studies. Glioma spheroids were placed in the middle of 24-well plates The area covered by the tumor cells migrating out from the spheroid explant was used as an index of cell migration. Two orthogonal diameters of each explant area were measured daily using a phase contrast microscope over a 7 day period and the mean area covered by tumor cells was calculated. Migration assays were performed in quadruplicate.

1.12 Invasion Assay

Fetal rat brain cell aggregates were generated according to a standardized procedure, which was described previously (Reference 40). Briefly, 18-day-old BD IX rat fetuses were removed by cesarean section. The brains were carefully dissected, minced, and serially trypsinized. After centrifugation, $1 \times 10^7$ cells (resuspended in medium) were seeded in agar-coated wells of a 24-well plate. After 2 days of reaggregation, spheroids were transferred to fresh wells (five to seven aggregates/well), where they matured for 18 to 21 days. By that time, mature brain aggregates had formed. Fetal rat brain aggregates and glioma spheroids represent standardized, primary, avascular brain and tumor masses that resemble brain and glioma tissues in situ, thus providing a suitable model to investigate glioma cell migration and vascular-independent invasion in vitro. For the invasion assay, single mature, brain aggregates (diameter=250-300 µm) were placed into agar-coated 96 well plates. Single glioma spheroids of similar size were also transferred into the wells and brought in contact with the brain aggregates. The confrontations were cultured for 24 and 48 h respectively, after which time they were harvested, fixed in paraformaldehyde and embedded into plastic resin for the preparation of semithin sections (2 µm). The sections where stained with Tolouidine blue. The process of glioma cell invasion was assessed for the amount of rat brain aggregate remaining intact. Invasion assays were performed in quadruplicate.

1.13 Statistics

For analysis of differences between the groups, one-way analysis of variance (ANOVA) followed by the appropriate post hoc test for individual comparisons between the groups was performed. Results with $p<0.05$ were considered significant.

2. Results 2.1

Figure 8:
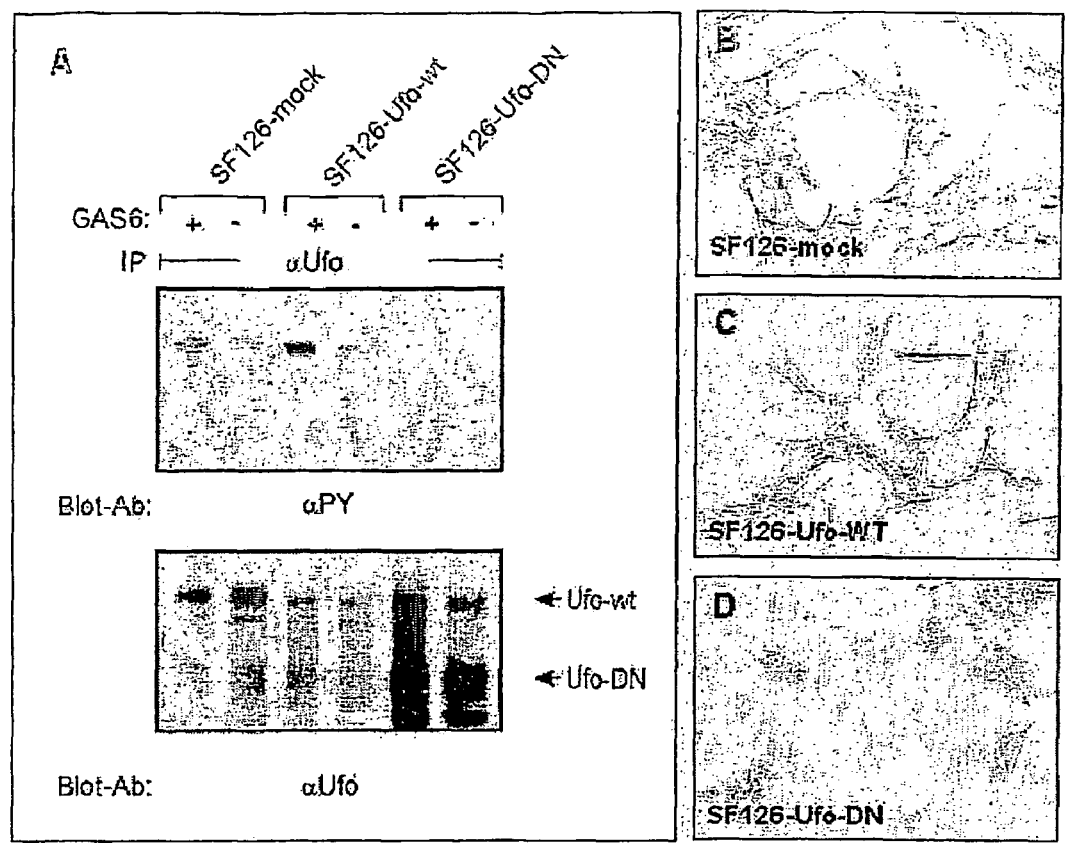

To study the relevance of UFO/AXL in glioma cell biology a truncated, dominant-negative mutant form of human UFO/AXL lacking the intracellular RTK-bearing domain, was introduced into SF126 glioma cells (SF 126-Ufo-DN) using a retroviral expression system. Cells transfected with an empty vector (SF126-mock) or human wild-type form of UFO/AXL (SF126-Ufo-WT) served as controls. Western blotting with an antibody directed against the extracellular domain of human UFO/AXL confirmed the high expression levels of the wild-type and truncated receptor in SF 126-Ufo-DN cell clones (FIG. 8A low panel). To ascertain whether the expression of the truncated receptor blocked UFO/AXL signal transduction, the UFO/AXL receptor phosphorylation following stimulation with its ligand Gas6 was determined (FIG. 8A top lane). In SF126-mock cells, a moderated baseline signal was observed which increased upon Gas6 stimulation. In SF126-Ufo-WT, the Gas6-induced signal was increased. In contrast, in SF126-Ufo-DN cells, both baseline and Gas6-induced phosphorylation were almost completely suppressed.

Blocking of UFO/AXL signalling had profound effects on glioma cell morphology, under regular culture conditions and in the absence of its ligand. While SF126-mock and SF126-UFO-WT cells (FIGS. 8B and C) displayed an elongated, spindle shaped morphology with multiple cell-to-cell contacts, SF126-UFO-DN cells were characterized by a round morphology and reduced cell-to-cell contacts (FIG. 8D). Also, SF126-UFO-DN cells appeared to have lost their ability to adhere well to plastic.

2.2

In order to study the relevance of UFO/AXL for tumor growth $1 \times 10^6$ cells of each clone were implanted subcutaneously into the flank of adult nude mice. When compared to SF126-mock cells the tumorigenicity of SF126-Ufo-DN cells was dramatically impaired, resulting in a 97% reduced tumor growth (FIG. 9A). In contrast, tumor growth was slightly accelerated in SF126-Ufo-WT cells (FIG. 9A). In order to obtain a more detailed insight into the role of UFO/AXL in glioma cell biology in vivo, SF126-Ufo-WT cells and SF126-Ufo-DN cells were implanted into the dorsal skinfold transparent chamber model of adult nude mice. Following fluorescent labeling of tumor cells and systemic administration of fluorescent plasma markers, this model allows for a repeatable and non-invasive assessment of tumor growth, tumor cell behavior, tumor angiogenesis and tumor perfusion by intravital multi-fluorescence videomicroscopy. Using this approach the significance of UFO/AXL signalling for tumor growth could be confirmed.

In comparison to SF126-Ufo-WT tumors, expansion of SF126-Ufo-DN tumors was significantly suppressed (FIG. 9B). One mechanism by which UFO/AXL may influence tumor growth and expansion is its modulation of blood vessel function and nutritive blood supply to the tumor. This hyothesis is supported by recent studies suggesting that Gas6/UFO/AXL-mediated signalling may interfere with the coagulation cascade as well as with blood vessel formation and maturation (Reference 41, 42). To test this, the tumors' functional vessel density and microvessel diameter as markers of tumor angiogenesis and tumor perfusion were quantitatively analyzed. However, as illustrated in FIG. 9B, these analyses failed to support a vascular explanation (e.g. anti-angiogenesis, perfusion failure due to, tumor vessel thrombosis) for the dramatic inhibition of SF126-Ufo-DN tumor growth.

Figure 9:
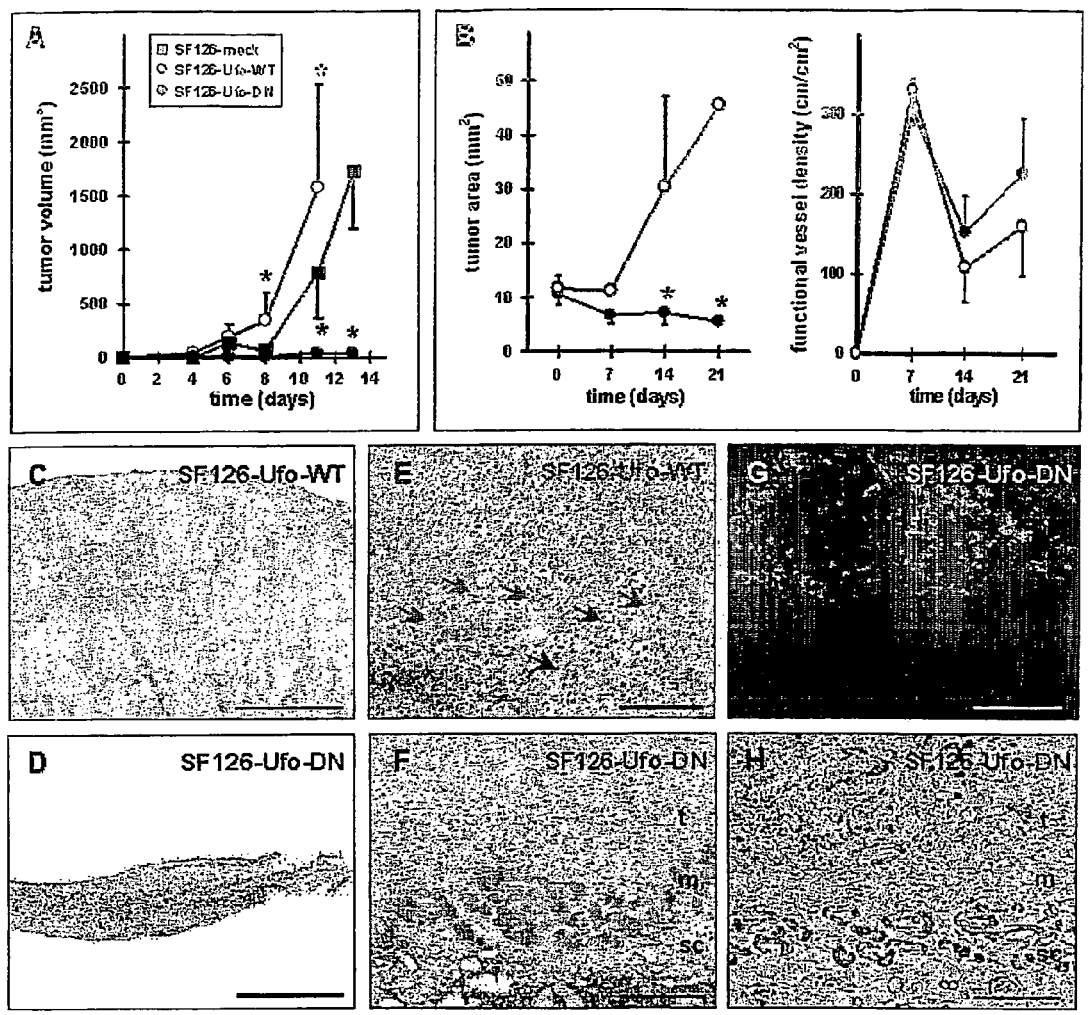

The histomorphological analysis of the tumor specimens further emphasized the hypothesis that UFO/AXL signalling plays a central role for glioma cell biology. As demonstrated in FIGS. 9C and E, SF126-Ufo-WT tumors were characterized by a large solid tumor mass as well as massive invasion and subsequent destruction of the adjacent host tissue (i.e.

muscle and subcutaneous tissue) by individual tumor cells. In contrast, SF126-Ufo-DN tumors were much smaller and failed to invade into the surrounding host tissues (FIGS. 9 D and F). This lack of SF126-Ufo-DN tumor invasion tissue was further confirmed by fluorescence and phase contrast microscopy of frozen sections demonstrating lack of Dil-labeled SF126-Ufo-DN cells within the adjacent tissue (FIGS. 9 G and H).

2.3

Figure 10:
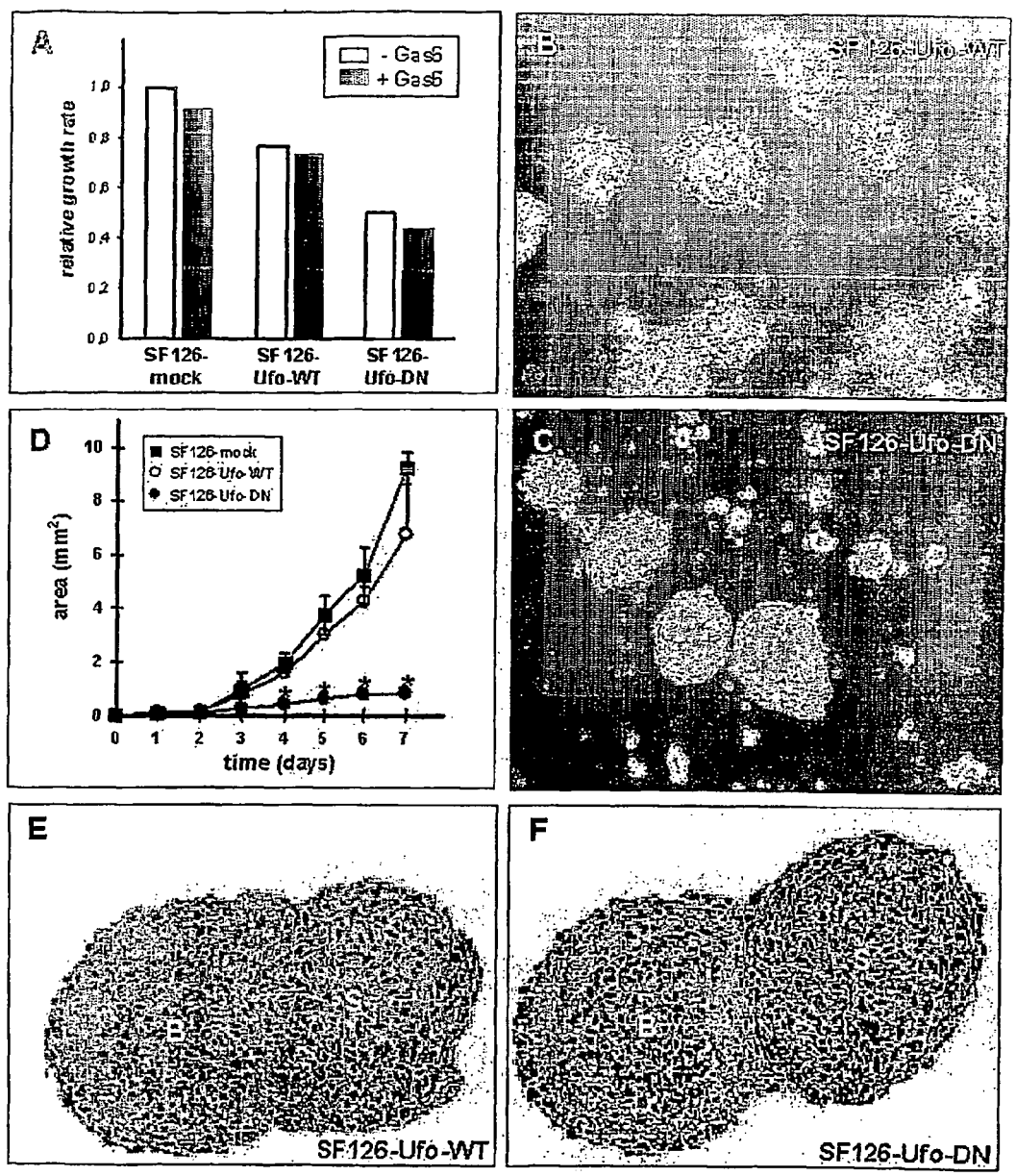

In order to further reveal the mechanisms underlying suppression of tumor growth via blocking of UFO/AXL function, glioma cell behavior in vitro was analyzed. MTT assays demonstrated that proliferation of SF126-Ufo-DN cells under regular culture conditions was reduced by 50% and 35% when compared to SF126-mock and SF126-Ufo-WT cells, respectively (FIG. 10A). Noteworthy this result was independent of stimulation with the UFO/AXL ligand Gas6, which confirms the previous hypothesis that Gas6/Ufo/AXL signalling does not exert a mitogenic activity. Since UFO/AXL has been suggested to mediate cell-call adhesion (Reference 43) the cells ability to form multicellular aggregates was also studied. SF126-mock and SF126-Ufo-WT cells readily formed spheroids (FIG. 10B). Their ability to aggregate was not attenuated in SF126-Ufo-DN cells (FIG. 10C) which confirms that cell aggregation is mediated solely by the extracellular domain of UFO/AXL, independent of the tyrosine kinase domain. Next, glioma cell migration was addressed by plating the tumor spheroids and measuring the distance of migrating tumor cells from the originating spheroid over time. While SF126-mock and SF126-Ufo-WT cells migrated comparable distances, tumor cell migration was severely impaired in SF126-Ufo-DN cells (FIG. 10D). Since cell migration is a prerequisite for tumor invasion the invasiveness of the SF126 cell clones was finally addressed by confronting tumor spheroids with fetal rat brain cell aggregates. Following 48 hours of co-culture, both SF126-mock and SF126-Ufo-WT cells had diffusely invaded the brain aggregate (FIG. 10E). In contrast, after the same time period a clear border between the SF126-Ufo-DN tumor spheroid and the brain cell aggregate could be observed, indicating that these cells were unable to invade into normal brain tissue (FIG. 10F).

Figure 11:
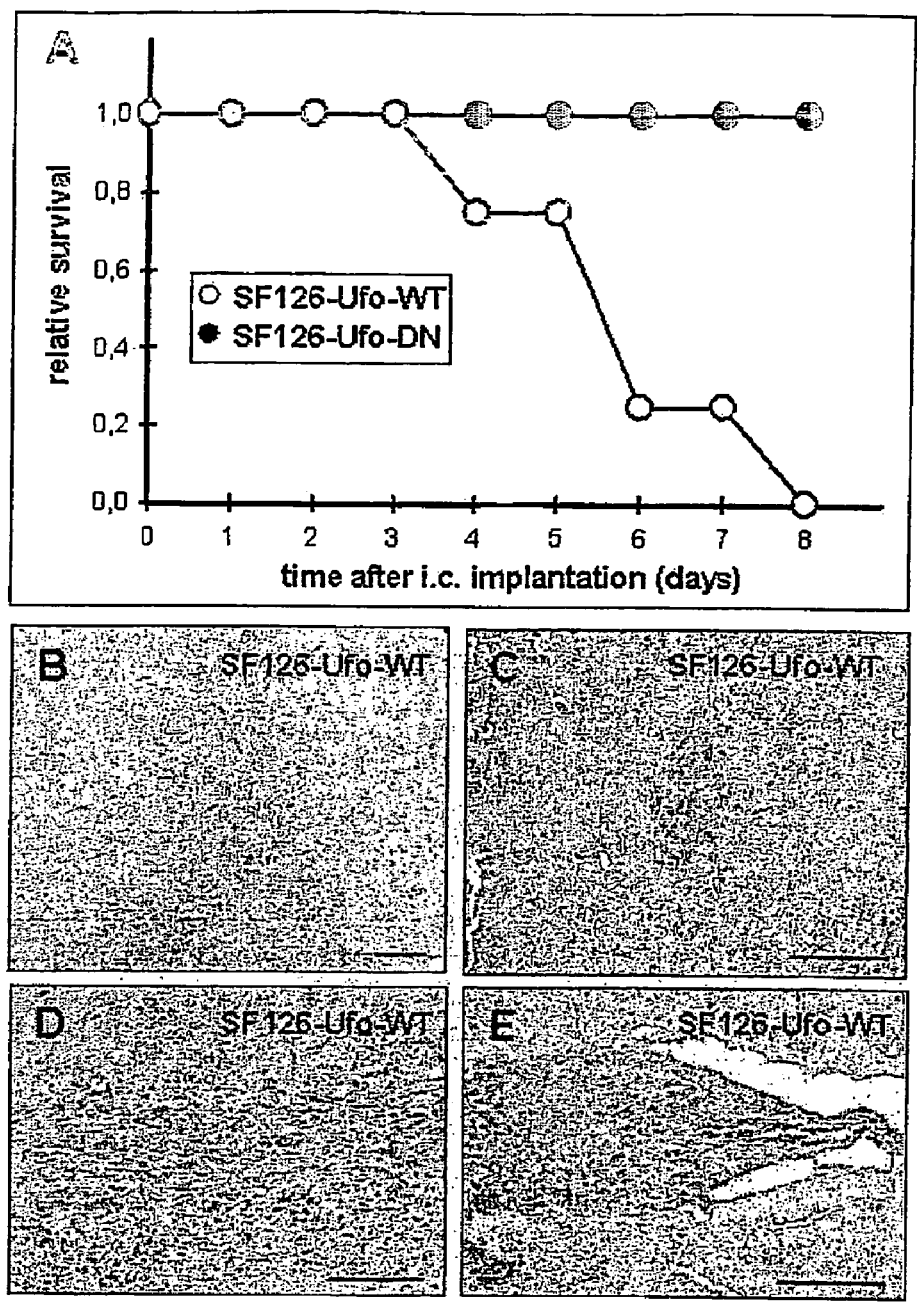

Collectively, the histomorphology of the tumor xenografts and the present in vitro results provided clear evidence that UFO/AXL significantly modulates growth, migration and invasion of glioma cells and that inhibition of UFO/AXL signalling suppresses tumor expansion by blocking tumor cell growth and invasion into the adjacent tissue. To test the ability of UFO/AXL for being a novel target for the treatment of malignant glioma SF126-Ufo-WT cells and SF126-Ufo-DN cells were implanted into the brains of adult nude mice and their survival was assessed. Animals were sacrificed as soon as they developed neurological deficits or lost >30% of their initial body weight. SF126-Ufo-WT tumors were characterized by an aggressive clinical course in that all animals had to be sacrificed within 8 days due to a rapid clinical deterioration (FIG. 11A). In contrast, animals bearing SF126-Ufo-DN tumors survived for the same observation period symptom-free and without weight loss (body weight day 0=29±2 g versus body weight day 8=28±1 g) (FIG. 11A). The histomorphological analysis revealed that SF126-Ufo-WT cells had diffusely infiltrated the brain parenchyma while the space occupying effect of the solid tumor mass was only moderate (FIG. 11B). Here, the typical means of human tumor cell invasion could be observed: along the perivascular space (FIG. 11C), along white matter tracts (FIG. 11D), and along the wall of the ventricular system (FIG. 11E). In contrast, SF126-Ufo-DN tumor formation could not be identified in any of the animals.

2.4. Summary

In summary, the results of the present analyses suggest a novel fundamental role for the RTK UFO/AXL in the biology of malignant brain tumors. The findings indicate that UFO/AXL is overexpressed by a significant number of human glioma cell lines, to an extent that is comparable to EGFR or PDGFR-α, and that it mediates glioma growth as well as glioma invasion. So far, UFO/AXL is the first RTK reported to be involved in glioma invasion and, therefore, represents a novel therapeutic target for interfering with these highly aggressive, as yet therapy-refractory, tumors. This is supported by the present results which demonstrate that inhibition of UFO/AXL signalling suppresses glioma growth and prolongs survival following orthotopic implantation.

In order to study the biological function of UFO/AXL this complex ability of human glioma cells to interact with each other and the matrix was analyzed in detail. As a result it could be demonstrated that inhibition of UFO/AXL function by expressing a truncated dominant-negative receptor mutant almost completely suppresses the cells ability to migrate and to invade into healthy brain tissue. It should be noted that the mutant form of UFO/AXL that was utilized in the present experiments lacked the intracellular domain, with the extracellular domain still being functionally intact. Consequently, UFO/AXL does not mediate tumor cell invasion simply through an interaction of the receptor with the matrix, but rather through involving the complex signalling cascade downstream the receptor. Furthermore, the present results also suggest that UFO/AXL is involved in tumor cell proliferation, potentially again through modulating cell-cell and cell-matrix interactions.

The central nervous system is characterized by a prominent expression of UFO/AXL, its ligand Gas6, and related RTKs, such as Tyro 3 or Mer. The findings of the present study now indicate that Gas6/UFO/AXL signalling may be part of the molecular system orchestrating migration and guidance of neurons and glial cells. Furthermore, the prominent expression of UFO/AXL and its ligand Gas6 by both the host and tumor tissue may provide a clue to a better understanding of the unique invasive capacity of tumors originating within the brain.

C. Discussion

The fact that RTK AXL as a single gene is sufficient to induce tumor metastasis in experimental systems is surprising, because it stands in contrast to the current view that the acquisition of a metastatic phenotype is a multistep process involving several genetic and epigenetic events.

Both benign and malignant tumours grow in an uncontrolled way. But only cells of malignant tumours invade surrounding tissues and travel to distant organs (metastasize). An understanding of the molecular basis for this aggressiveness could lead to therapies that block the transition of a tumour from benign to malignant, and keep local disease in check. We have now identified proteins called. AXL and GAS as a receptor-ligand pair in a molecular checkpoint that regulates not only the invasiveness but also the surviving and movement of tumour cells—the trio of characteristics required for metastasis. The dn-AXL/GAS6 complex also suppresses tumor cells anti-apoptotic capability.

The present data show that GAS treatment of the BT-549 cells (stable expression of dn-AXL) in the presence of serum is not able to induce activation of ERK1/2 MAPK. Thus, this signalling pathway is effectively blocked AXL suppression.

In summary, the present data have shown that AXL/GAS play a key role in human cancers by influencing tumor cell invasion. AXL protein is a new target for cancer diagnosis and treatment (anti-invasiveness). For example, expression of dnAXL in cancer cells can prevent them from invasion and development of metastases. Further, genes of AXL-cluster (listed in Tab. 2) can be used as diagnostic tool for, the detection of the pre-invasive stage development in primary tumours, particularly in primary tumours of breast, prostate, kidney and glioblastomas.

D. Conclusions

1. Using cDNA array analysis of BC cell lines, primary tumors and glioblastoma cells a "consensus of, invasiveness" (cluster AXL) has been identified. This consensus of invasiveness, comprising 32 genes, can be used to predict the aggressiveness of cancer cells and primary tumors.

2. A dominant negative mutant of AXL (dn-AXL) strongly suppresses the invasion of highly invasive breast cancer cell lines and also increases their sensitivity to serum withdrawal (apoptosis). A polyclonal antibody directed against extracellular portion of AXL (containing amino acids residues 1-410, Ex-AXL), is able to suppress the aggressiveness of the treated cancer cells.

3. RTK AXL as a single gene is sufficient to induce breast cancer call invasiveness in experimental systems (see 2 and data on model systems BC-MCF7-wt AXL and prostate cancer cell line-LNCaP-wt AXL). This result is in contrast to the current view that the acquisition of a metastatic phenotype is a multistep process involving several genetic and epigenetic events.

4. RTK AXL is a good candidate for "Signal-transduction therapy" treatment strategies in which key pathways for hyperactive cellular signalling that cause cancer invasiveness and metastasis are targeted. The suppression of AXL signalling function by a dn-AXL mutant and/or by treatment with an inhibitory antibody cannot be bypassed by collateral or compensatory pathways.

5. Suppression of AXL gene expression in tumor therapy may be carried out by inhibition of AXL on the gene or transcript level, e.g. gene transfer of mutants, antisense molecules, ribozymes, siRNA, RNAi, or AXL gene expression supressors or on the protein level, e.g. by low molecular weight AXL kinase inhibitors, AXL analogues, e.g. Ex-AXL fusion proteins such as a fusion of Ex-AXL with an JgG1 Fc fragment (ref. 32) or inhibitory antibodies. Further, suppression of AXL gene expression may be effected by AXL signal inhibitors, e.g. downstream inhibitors.

TABLE 2

Consensus of invasiveness.

Breast cancer cell lines and control

| No | Genes of AXL cluster | Known function or involvement |
|---|---|---|
| 1 | AXL/GAS | proliferation, adhesion, antiapoptotic function, not yet associated with invasion |
| 2 | HBEGF | heparin-binding EGF |
| 3 | EPHA2 | involved in breast cancer, prostate cancer, melanomas, glioblastomas, vascularization |
| 4 | S6KII | STK, ribosomal S6 kinase 2, not yet associated with invasion |
| 5 | SGK | STK, glucocorticoid-regulated kinase, antiapoptotic function, involved in survival of cells |
| 6 | ADAM17 | TACE involved in shedding of TNF alpha receptor |
| 7 | Lyn/Fyn | SRC-family kinases |
| 8 | MAP4K4 | STK, activates JNK (but not p38 and ERKs), may be involved in TNFalpha signalling, similar to SLK |
| 9 | CD44/META1 | marker of cancer cells invasiveness |
| 10 | ADAM12 | interacts with integrins, coexists with SRC and GRB2 in membrane ruffles, cytopl.domain involved in signalling via SH3 |
| 11 | Caveolin 1, 2 | key role in signalling, associated with cell transformation, promote cell invasion |
| 12 | M-CSF | ligand for CSF-R1, vasculogenesis, constitutivelly expressed by invasive breast cancer cells |
| 13 | MMP14 | unic expression in endothelial cells, specific for CD44 shedding |
| 14 | Vimentin | associated with cell transformation, promotes cell migration and invasion, marker of epithelial-mesenchymal transition of cancer cells |
| 15 | SIRP alpha | adhesion, signalling, migration, involvement in invasion is unknown |

TABLE 3

| NO | Spot labels(HUGO classification) | Accession | GenBank/Ink | Publication |
|---|---|---|---|---|
| 1 | AXL (AXL receptor.tyrosine kinase) | M76125 | M76125 | Mol. Cell. Biol. 11(10), 5016-5031 (1991) |
| 2 | ADAM12 (a disintegrin and metalloproteinase domain 12 = meltrin alpha) | AF023476 | AF023476 | J. Biol, Chem. 273 (1), 157-166 (1998) |
| 3 | ADAM17 (a disintegrin and metalloproteinase domain 17 = TACE) | U69611 | U69611 | Nature 385 (6618), 729-733 (1997) |
| 4 | ANXA2 (Annexin A2, p35 src-binding) | D00017 | D00017 | Cell 46 (2), 191-199 (1986) |
| 5 | CAV1 (caveolin 1, caveolae protein, 22 kD) | Z18951 | Z18951 | FEBS Lett, 314 (1), 45-48 (1992) |
| 6 | CAV2 (caveolin 2) | AF035752 | AF035752 | Proc. Nati. Acad. Sci. U.S.A. 93 (1), 131-135 (1996) |
| 7 | CD44 (antigen = involved in matrix adhesion) | X66733 | X66733 | J. Invest. Dermatol. 99, 381-385 (1992) |
| 8 | DDR2 (discoidin domain receptor family, member 2) | X74764 | X74764 | Oncogene 8 (12), 3433-3440 (1993) |
| 9 | FGF2 (fibroblast growth factor 2 (basic)) | NM002006 | NM 002006 | EMBO J. 5 (10), 2523-2528 (1986) |
| 10 | FGF5 (fibroblast growth factor 5) | NM004464 | NM 004464 | Mol. Cell. Biol. 8 (8), 3487-3495 (1988) |
| 11 | EPHA2 (EphA2 = ephrin type-a receptor 2L) | M59371 | M59371 | Mol. Cell. Biol. 10 (12), 6316-6324 (1990) |
| 12 | GAS6 (AXL ligand, growth arrest-specific 6) | L13720 | L13720 | Mol. Cell. Biol. 13 (8), 4976-4985 (1993) |
| 13 | FRK (fyn-ralated kinase) | U00803 | U00803 | Gene 138, 247-251 (1994) |
| 14 | (HB-EGF)DTR (heparin-binding epidermal growth factor-like growth factor) | NM001945 | NM 001945 | Science 251, 936-939 (1991) |
| 15 | LYN (tyrosine-protein kinase) | M16038 | M16038 | Mol. Cell. Blol. 7 (1), 237-243 (1987) |

TABLE 3-continued

| NO | Spot labels(HUGO classification) | Accession | GenBank/Ink | Publication |
|---|---|---|---|---|
| 16 | PTPNS1 (PTP, non-receptor type substrate 1) | Y10375 | Y10375 | Nature 386 (6621), 181-186 (1997) |
| 17 | MMP1 (matrix metalloproteinase 1 = Interstitial collagenase) | M13509 | M13509 | J. Biol. Chem. 261, 6600-6605 (1986) |
| 18 | MMP14 (matrix metalloproteinase 14 (membrane-inserted)) | NM004995 | NM 004995 | Nature 370 (6484), 61-65 (1994) |
| 19 | MMP2 (matrix metalloproteinase 2, gelatinase A) | NM004530 | NM 004530 | J. Biol. Chem. 263, 6579-6587 (1988) |
| 20 | MMP9 (matrix metalloproteinase 9 = gelatinase B) | NM004994 | NM 004994 | J. Biol. Chem. 264 (29), 17213-17221 (1989) |
| 21 | MAP4K4(mitogen-activated protein kinase kinase kinase kinase 4) | XM038748 | NT 022171 | Direct Submission |
| 22 | MT3MMP, or MMP16 (matrix metalloproteinase 16 (membrane-inserted)) | NM005941 | XM 042409 | J. Biol. Chem. 270 (39), 23013-23020 (1995) |
| 23 | TIMP1 (tissue inhibitor of metalloproteinase 1) | NM003254 | NM 003254 | Nature 315 (6022), 768-771 (1985) |
| 24 | VIM (vimentin) | X56134 | X56134 | Nucleic Acids Res. 18 (22), 6692 (1990) |
| 26 | SGK (serum/glucocorticoid regulated kinase) | Y10032 | Y10032 | Proc. Natl. Acad. Sci. U.S.A. 94(9), 4440-4445 (1997) |
| 26 | RPS6KB1 (ribosomal protein S6 kinase, 70 kD, polypeptide 1) | M60724 | M60724 | Mol. Cell. Biol. 11, 5541-5550 (1991) |
| 27 | FYN (proto-oncogene tyrosine-protein kinase (syn) | M14333 | M14333 | Proc. Nati. Acad. Sci. U.S.A. 83, 5459-5463 (1986) |

TABLE 4

Expression of EGFR and UFO/Axl in human glioma cell lines as assessed by tyrosin kinase cDNA array

| cell line | EGFR | UFO/Axl | UFO/Axl:EGFR |
|---|---|---|---|
| U-118 | 169 | 1793 | 10.6 |
| U-1242 | 324 | 1793 | 5.5 |
| SF126 | 296 | 1612 | 5.4 |
| A-172 | 438 | 1935 | 4.4 |
| U-373 | 56 | 190 | 3.4 |
| U-1240 | 139 | 262 | 1.9 |
| T-98G | 540 | 800 | 1.5 |
| SF763 | 5526 | 39 | 0.0 |
| SF767 | 1039 | — | 0.0 |

REFERENCES

1. J. W. Janssen, A. S. Schulz, A. C. Steenvoorden et al., A novel putative tyrosine kinase receptor with oncogenic potential. Oncogene 6 (1991), pp. 2113-2120.
2. J. O'Bryan, R. A. Frye, P. C. Cogswell et al., AXL, a transforming gene isolated from primary human myeloid leukemia cells, encodes a novel receptor tyrosine kinase. Mol. Cell. Biol. 11 (1991), pp. 5016-5031.
3. Healy, A. M., Schwartz, J. J., Zhu, X., Herrick, B. E., Varnum, B., Farber, H. W. (2001). Gas 6 promotes AXL-mediated survival in pulmonary endothelial cells. Am. J. Physiol. 280: 1273L-1281.
4. A. Neubauer, A. Fiebeler, D. K. Graham et al., Expression of axl, a transforming receptor tyrosine kinase, in normal and malignant hematopoiesis. Blood 84(1994), pp. 1931-1941.
5. P. McCloskey, J. Pierce, R. A. Koski, B. Varnum and E. T. Liu, Activation of the AXL receptor tyrosine kinase induces mitogenesis and transformation in 32D cells. Cell Growth Differ. 5 (1994), pp. 1105-1117.
6. P. Bellosta, Q. Zhang, S. P. Goff and C. Basilico, Signalling through the ARK tyrosine kinase receptor protects from apoptosis in the absence of growth stimulation. Oncogene 15 (1997), pp. 2387-2397.
7. S. Goruppi, E. Ruaro and C. Schneider, Gas6, the ligand of AXL tyrosine kinase receptor, has mitogenic and survival activities for serum starved NIH3T3 fibroblasts. Oncogene 12 (1996), pp. 471-480.
8. P. McCloskey, Y. W. Fridell, E. Attar et al., GAS6 mediates adhesion of cells expressing the receptor tyrosine kinase AXL. J. Biol. Chem. 272 (1997), pp. 23285-3291.
9. Caron de Fromentel C., Nardeux P. C., Soussi T., Lavialle C., Estrade S., Carloni G., Chandrasekaran K., Cassingena R. Epithelial HBL-100 cell line derived from milk of an apparently healthy woman harbors SV40 genetic information. Exp. Cell Res., (1985), 160: 83-94.
10. Albini A., Iwamoto Y., Kleinman H. K., Martin G. R., Aaronson S. A., Kozlowski J. M., McEwan R. N. A rapid in vitro assay for quantitating the invasive potential of tumor cells. Cancer Res., 47: 3239-3245, 1987.
11. Thompson E. W., Paik S., Brunner N., Sommers C. L., Zugmaier G., Clarke R., Shima T. B., Torri J., Donahue S., Lippman M. E., et al Association of increased basement membrane invasiveness with absence of estrogen receptor and expression of vimentin in human breast cancer cell lines. J. Cell. Physiol., 150:534-544, 1992.
12. Terranova V. P., Hujanen E. S., Martin, G. R. Basement membrane and the invasive activity of metastatic tumor cells. J. Natl. Cancer Inst. (Bethesda), 77: 311-316, 1986.
13. Perou C. M., Jeffrey S. S., van de Rijn M., Rees C. A., Eisen M. B., Ross D. T., Pergamenschikov A Williams C. F., Zhu S. X., Lee J. C., Lashkari D., Shalon D., Brown P. O., Botstein D. Distinctive gene expression patterns in human mammary epithelial cells and breast cancers. Proc. Natl. Acad. Sci. USA, 96: 9212-9217, 1999.
14. Perou C. M., Sorlie T. Eisen M. B., van de Rijn M., Jeffrey S. S., Rees C. A., Pollack J. R., Ross D. T., Johnsen H., Akslen L. A., Fluge O., Pergamenschikov A., Williams C., Zhu S. X., Lonning P. E., Borresen-Dale A. L., Brown P. O., Botstein D. Molecular portraits of human breast tumours. Nature (Lond.), 406: 747-752, 2000.
15. Johnston M. Gene chips: array of hope for understanding gene regulation. Curr. Biol., 8: R171-174, 1998.
16. Duggan D. J., Bittner M., Chen Y., Meltzer P., Trent J. M. Expression profiling using cDNA microarrays. Nat. Genet., 21: 10-14, 1999.
17. Price J. E., Polyzos A., Zhang R. D., Daniels L. M. Tumorigenicity and metastasis of human breast carcinoma cell lines in nude mice. Cancer Res., 50: 717-721, 1990.
18. Sommers C. L., Byers S. W., Thompson E. W., Torri J. A., Gelmann E. P. Differentiation state and invasiveness of human breast cancer cell lines. Breast Cancer Res. Treat, 31: 325-335, 1994.

19. Deborah A. Zajchowski, Marty F. Bartholdi, Yan Gong, Lynn Webster, Hsiao-Lai Liu, Alexander Munishkin, Catherine Beauheim, Susan Harvey, Stephen P. Ethier and Paul H. Johnson. Identification of Gene Expression Profiles That Predict the Aggressive Behavior of Breast Cancer Cells. Cancer Research 61, 5168-5178, Jul. 1, 2001.
20. A. Wimmel, M. Schilli, U. Kaiser et al., Preferential histiotypic expression of CD44-isoforms in human lung cancer. Lung Cancer 16 (1997), pp. 151-172.
21. Subburaj Ilangumaran, Anne Briol, and Daniel C. Hoessli. CD44 Selectively Associates With Active Src Family Protein Tyrosine Kinases Lck and Fyn in Glycosphingolipid-Rich Plasma Membrane Domains of Human Peripheral Blood Lymphocytes. Blood, Vol. 91 No. 10 (May 15), 1998: pp. 3901-3908
22. Domagala W., Lasota J., Bartowiak J., Weber K., Osborn M. Vimentin is preferentially expressed in human breast carcinomas with low estrogen receptor and high Ki-67 growth fraction. Am. J. Pathol., 136: 219-227, 1990.
23. Domagala W., Wozniak L., Lasota J., Weber K., Osborn M. Vimentin is preferentially expressed in high-grade ductal and medullary but not in lobular breast carcinomas. Am. J. Pathol., 137: 1059-1064, 1990.
24. Hayashi K, Matsuda S, Machida K, Yamamoto T, Fukuda Y, Nimura Y, Hayakawa T, Hamaguchi M. Invasion activating caveolin-1 mutation in human scirrhous breast cancers. Cancer Res 2001 March 15; 61(6):2361-4.
25. Yang G, Truong L D, Timme T L, Ren C, Wheeler T M, Park S H, Nasu Y, Bangma C H, Kattan M W, Scardino P T, Thompson T C. Elevated expression of caveolin is associated with prostate and breast cancer. Clin Cancer Res 1998 August; 4(8):1873-80.
26. Bachmeier B E, Nerlich A G, Lichtinghagen R, Sommerhoff C P. Matrix metalloproteinases (MMPs) in breast cancer cell lines of different tumorigenicity. Anticancer Res 2001 November-December; 21(6A):3821-8.
27. Sounni N E, Devy L, Hajitou A, Frankenne F, Munaut C, Gilles C, Deroanne C, Thompson E W, Foidart J M, Noel A. MT1-MMP expression promotes tumor growth and angiogenesis through an up-regulation of vascular endothelial growth factor expression. FASEB J 2002 April; 16(6):555-64.
28. Lin E Y, Nguyen A V, Russell R G, Pollard J W. Colony-stimulating factor 1 promotes progression of mammary tumors to malignancy. J Exp Med 2001 March 19; 193(6): 727-40.
29. Pederson L, Winding B, Foged N T, Spelsberg T C, Oursler M J. Identification of breast cancer cell line-derived paracrine factors that stimulate osteoclast activity. Cancer Res 1999 November 15; 59(22):5849-55.
30. Kelly Carles-Kinch, Katherine E. Kilpatrick, Jane C. Stewart and Michael S. Kinch. Antibody Targeting of the EphA2 Tyrosine Kinase Inhibits Malignant Cell Behavior. Cancer Research 62, 2840-2847, May 15, 2002.
31. Bange J., Prechtl D., Cheburkin Y., Specht K., Harbeck N., Schmitt M., Knyazeva T., Muller S., Gartner S., Sures I., Wang H., Imyanitov E., Haring H U, Knyazev P., Iacobelli S., Hofler H., Ullrich A. Cancer progression and tumor cell motility are associated with the FGFR4 Arg (388) allele. Cancer Res. 2002, February 1, 62(3), 840-7.
32. Yanagita M., Arai H., Ishii K., Nakano T., Ohashi K., Mizuno K., Varnum B., Fukatsu A., Doi T., Kita T. Gas6 regulates mesangial cell proliferation through AXL in experimental glomerulonephritis. Am. J. Pathol, 2001 April; 158(4), 1423-32.
33. Attar E. C, Fridell Y. C, Xu L., Jin Y., Maia D. M., Schell M. J., and Liu E. T. AXL receptor tyrosine kinase expression in human breast cancer. Breast Cancer Research and Treatment, (October, 1997) Vol. 46, No. 1, pp. 91.
34. Dodge Zantek N., Walker-Daniels J., Stewart J., Hansen R., Robinson D., Miao H., Wang B., Kung H-J., Bissell M. J. and Kinch M. MCF-10A-neoSt: A New Cell System for Studying Cell-ECM and Cell-Cell Interactions in Breast Cancer. Clinical Research, Vol. 7, 3640-3548, November 2001.
35. Vajkoczy, P., Goldbrunner, R., Farhadi, M., Vince, G., Schilling, L., Tonn, J. C., Schmiedek, P., and Menger, M. D. Glioma cell migration is associated with glioma-induced angiogenesis in vivo, Int J Dev Neurosci. 17: 557-63, 1999.
36. Sasaki, T., Knyazev, P. G., Cheburkin, Y., Gohring, W., Tisi, D., Ullrich, A., Timpl, R., and Ho-henester, E. Crystal structure of a C-terminal fragment of growth arrest-specific protein-Gas6. Receptor tyrosine kinase activation by laminin G-like domains, J Biol Chem. 277: 44164-70, 2002.
37. Vajkoczy, P., Schilling, L., Ullrich, A., Schmiedek, P., and Menger, M. D. Characterization of angiogenesis and microcirculation of high-grade glioma: an intravital multifluorescence micro-scopic approach in the athymic nude mouse, J Cereb Blood Flow Metab. 18: 510-520, 1998.
38. Vajkozy, P., Farhadi, M., Gaumann, A., Heidenreich, R., Erber, R., Wunder, A., Tonn, J. C., Menger, M. D., and Breier, G. Microtumor growth initiates angiogenic sprouting with simultaneous expression of VEGF, VEGF receptor-2, and angiopoietin-2, J Clin Invest. 109: 777-85, 2002.
39. Read, T. A., Farhadi, M., Bjerkvig, R., Olsen, B. R., Rokstad, A. M., Huszthy, P. C., and Vajko-czy, P. Intravital microscopy reveals novel antivascular and antitumor effects of endostatin delivered locally by alginate-encapsulated cells, Cancer Res. 61: 6830-7, 2001.
40. Bjerkvig, R., Laerum, O. D., and Mella, O. Glioma cell interactions with fetal rat brain aggregates in vitro and with brain tissue in vivo, Cancer Res. 46: 4071-9, 1986.
41. Stitt, T. N., Conn, G., Gore, M., Lai, C., Bruno, J., Radziejewski, C., Mattsson, K., Fisher, J., Gies, D. R., Jones, P. F., and et al. The anticoagulation factor proteins and its relative, Gas6, are ligands for the Tyro 3/Axl family of receptor tyrosine kinases, Cell. 80: 661-70, 1995.
42. Fridell, Y. W., Villa, J., Jr., Attar, E. C., and Liu, E. T. GAS6 induces Axl-mediated chemotaxis of vascular smooth muscle cells, J Biol Chem. 273: 7123-6, 1998.
43. Bellosta, P., Costa, M., Lin, D. A., and Basilico, C. The receptor tyrosine kinase ARK mediates cell aggregation by homophilic binding, Mol Cell Biol. 15: 614-25, 1995.
44. Millauer B, Shawver L K, Plate K H, Risau W, Ulrich A (1994) Glioblastoma growth inhibited in vivo by a dominant-negative Flk-1 mutant. Nature (Lond.) 367: 576-579.

The invention claimed is:

1. A method of reducing the invasivity of cancer cells in a subject in need thereof comprising administering to the subject an inhibitor of the AXL protein or GAS6, or any combination thereof, in an amount which is effective for reducing the invasivity of cancer cells, and wherein said inhibitor of the AXL protein is selected from the group consisting of anti-AXL antibodies or Fab, Fab', Fab2 or scFV antigen binding fragments thereof, and wherein said inhibitor of GAS6 is selected from the group consisting of anti-GAS6 antibodies or Fab, Fab', Fab2 or scFV antigen binding fragments thereof, and wherein said cancer cells are selected from the group consisting of kidney cancer cells and glioblastoma cells.

2. The method of claim 1, wherein said inhibitor inhibits the receptor tyrosine kinase activity of the AXL protein.

3. The method of claim 1, wherein the inhibitor of the AXL protein inhibits the interaction between the AXL protein and its ligands.

4. The method of claim 1, wherein the cancer cells are glioblastoma cells.

5. The method of claim 1, wherein the subject is a mammal.

6. The method of claim 1, wherein the AXL protein inhibitor is an antibody directed against the AXL protein.

7. The method of claim 1, wherein the subject is a human.

8. The method of claim 1, wherein said inhibitor of GAS6 is further selected from the group consisting of Fab, Fab', Fab2, and scFV antigen binding fragments of the anti-GAS antibodies.

9. The method of claim 1, wherein said inhibitor inhibits AXL protein activity or the interaction between AXL protein and GAS6, or a combination thereof.

* * * * *

UNITED STATES PATENT AND TRADEMARK OFFICE
CERTIFICATE OF CORRECTION

| | | |
|---|---|---|
| PATENT NO. | : 8,277,802 B2 | Page 1 of 1 |
| APPLICATION NO. | : 10/521410 | |
| DATED | : October 2, 2012 | |
| INVENTOR(S) | : Ullrich et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 274 days.

Signed and Sealed this
Nineteenth Day of August, 2014

Michelle K. Lee
*Deputy Director of the United States Patent and Trademark Office*